(12) United States Patent
Kitchens et al.

(10) Patent No.: US 10,891,506 B2
(45) Date of Patent: Jan. 12, 2021

(54) SYSTEM AND METHOD FOR SUBDERMAL IMAGING

(71) Applicant: QUALCOMM Incorporated, San Diego, CA (US)

(72) Inventors: Jack Conway Kitchens, Town of Tonawanda, NY (US); John Keith Schneider, Williamsville, NY (US); Stephen Michael Gojevic, Lockport, NY (US); Evan Michael Breloff, Kenmore, NY (US)

(73) Assignee: QUALCOMM Incorporated, San Diego, CA (US)

( * ) Notice: Subject to any disclaimer, the term of this patent is extended or adjusted under 35 U.S.C. 154(b) by 337 days.

(21) Appl. No.: 16/002,939

(22) Filed: Jun. 7, 2018

(65) Prior Publication Data

US 2019/0377962 A1 Dec. 12, 2019

(51) Int. Cl.
*G06K 9/00* (2006.01)
*G01N 29/24* (2006.01)

(52) U.S. Cl.
CPC ..... *G06K 9/00906* (2013.01); *G01N 29/2418* (2013.01); *G01N 29/2437* (2013.01); *G06K 2009/00932* (2013.01)

(58) Field of Classification Search
CPC ..... G06K 9/00906; G06K 2009/00932; G01N 29/2418; G01N 29/2437; A61B 2562/0242; A61B 5/0095; A61B 5/6898; A61B 2562/0204; A61B 2562/046
See application file for complete search history.

(56) References Cited

U.S. PATENT DOCUMENTS

| 6,162,211 A | 12/2000 | Tankovich et al. |
| 10,366,269 B2 * | 7/2019 | Lu ................ G06K 9/00107 |
| 2007/0179365 A1 * | 8/2007 | Bitton .............. A61B 5/0059 600/310 |
| 2014/0100438 A1 * | 4/2014 | Wada ............... A61B 5/7246 600/407 |
| 2017/0323131 A1 | 11/2017 | Lu et al. |
| 2017/0323132 A1 | 11/2017 | Lu et al. |
| 2018/0068100 A1 * | 3/2018 | Seo .................. G06F 21/6218 |
| 2019/0377962 A1 * | 12/2019 | Kitchens ........... G01N 29/2418 |

FOREIGN PATENT DOCUMENTS

WO WO-2019236254 A1 * 12/2019 ........... A61B 5/0095

OTHER PUBLICATIONS

International Search Report and Written Opinion—PCT/US2019/032412—ISA/EPO—dated Aug. 19, 2019.

(Continued)

*Primary Examiner* — Daniel Pihulic
(74) *Attorney, Agent, or Firm* — Weaver Austin Villeneuve & Sampson LLP

(57) ABSTRACT

A subdermal imaging system which may determine whether a person's body is in contact with a display, and perform a subdermal imaging process to determine subdermal characteristics by a photoacoustic imaging process. Ultrasonic emissions emitted from the photoacoustic process may be received with an ultrasonic receiver array. The subdermal imaging system may adjust the wavelength and/or intensity of the photoacoustic process in order to image desired subdermal features.

26 Claims, 15 Drawing Sheets

(56) References Cited

OTHER PUBLICATIONS

Collinson P., "Barclays to Introduce 'Finger-Vein ID' Readers", Sep. 5, 2014, 1 Page.
Counter P.B., "Robocoin Chooses Fujitsu Palm Vein Biometrics for Bitcoin Kiosks", Sep. 10, 2014, 2 Pages.
"Forget Fingerprint Recognition—The Latest Anti-Cybercrime Measures Scan Your Veins", Sep. 8, 2014, 1 Page.
"Hitachi Reveals Finger Vein Solution for Online Shopping", Oct. 25, 2016, 1 Page.
Oberhaus D., "It Won't Be Difficult to Spoof Smartphone Finger Vein Scanners", Oct. 29, 2016, 2 Pages.
Perala A., "Fujitsu Launches Smart Origination Platform", Nov. 17, 2016, 1 Page.
Perala A., "Fujitsu Thinks Small with New F-Pro PalmSecure Sensor", Oct. 3, 2017, 1 Page.
Perala A., "GoVerifyID Integrated into SAP HANA Cloud Platform", Aug. 16, 2016, 1 Page.
Perala A., "Hitachi System Can Scan Finger Veins via Smartphone Camera", Oct. 25, 2016, 1 Page.
Perala A., "Honeywell Access Control Platform Enables Support for BioSec Palm Vein Authentication", Oct. 3, 2017, 1 Page.
Webber D., "Biometric Security: Giving Cyber Criminals the Finger", Sep. 16, 2014, 1 Page.

\* cited by examiner

*Figure 10D*
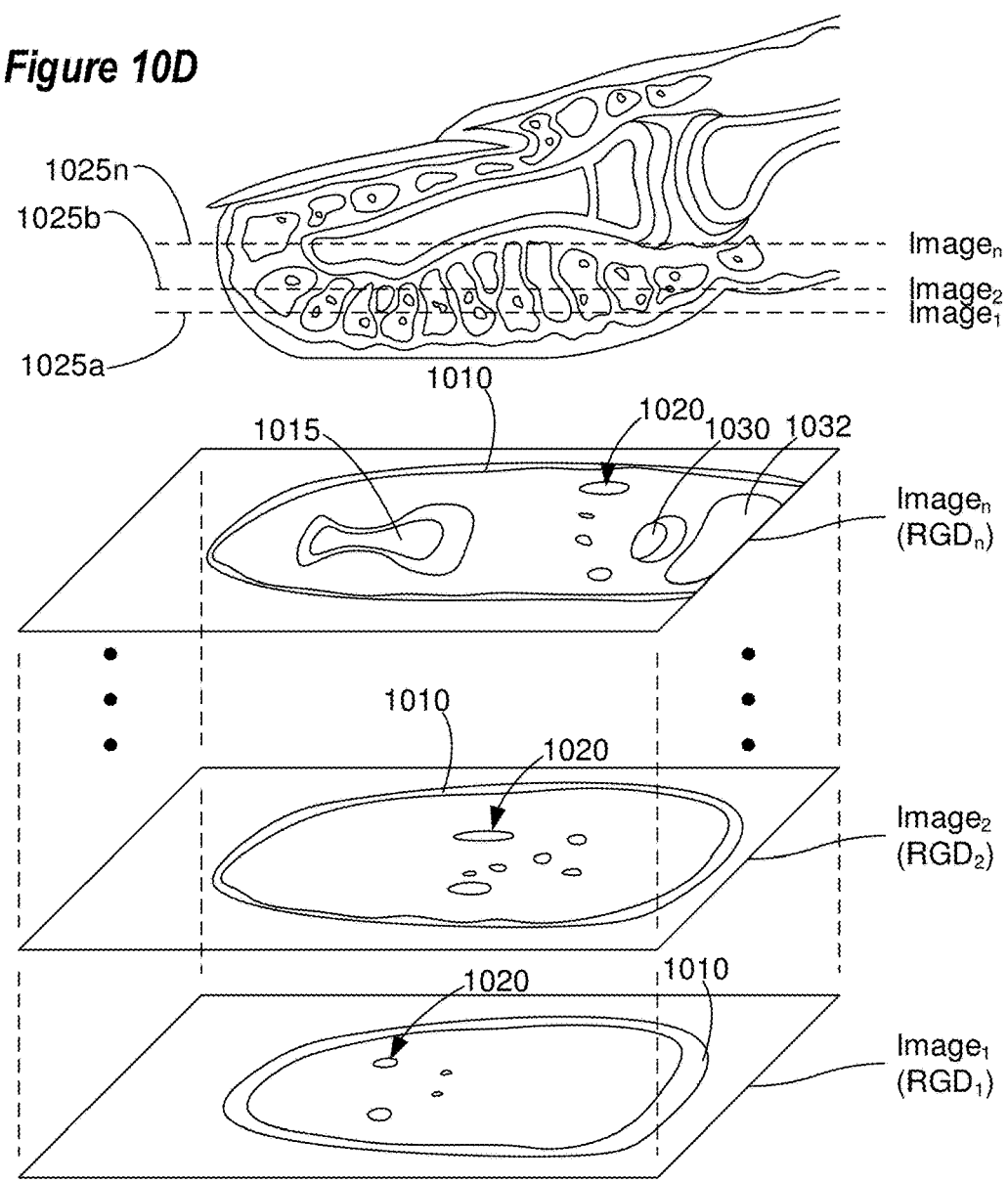
*Figure 10E*
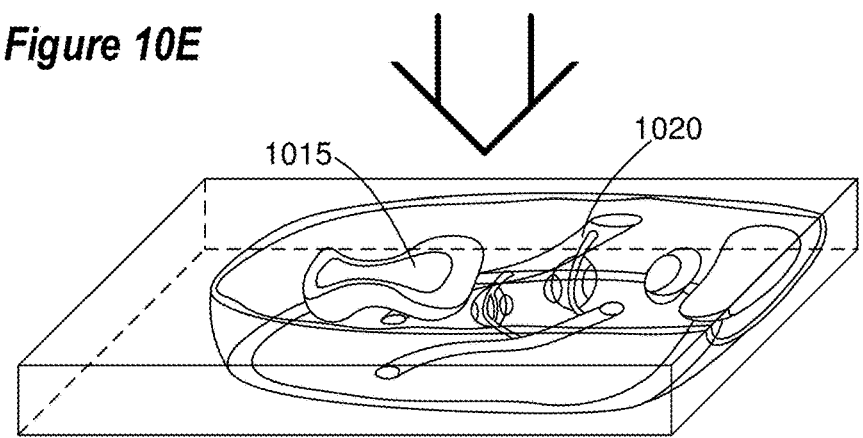
*Figure 10F*

SYSTEM AND METHOD FOR SUBDERMAL IMAGING

FIELD

This disclosure relates generally to subdermal imaging devices and methods, including but not limited to subdermal imaging devices and methods applicable to mobile devices.

BACKGROUND

Photoacoustic imaging has been performed to non-invasively map subdermal features in humans and animals. Light pulses are delivered into biological tissues, where some of the energy is absorbed by the tissue and converted into heat. This causes a transient thermoelastic expansion and contraction, which in turn causes an ultrasonic emission which may be measured. The characteristics of the ultrasonic emission reveals geometric aspects of the subdermal features.

Conventional photoacoustic imaging systems (also known as photoacoustic/thermoacoustic tomography) either use an unfocused ultrasound detector to acquire the photoacoustic signals and reconstruct an image by inversely solving the photoacoustic equations or use a focused ultrasound detector which scans by moving in a 2D matrix.

However, there is a need for improvements to these conventional systems.

SUMMARY

The systems, methods and devices of the disclosure each have several innovative aspects, no single one of which is solely responsible for the desirable attributes disclosed herein.

One innovative aspect of the subject matter described in this disclosure can be implemented in an apparatus. The apparatus may include a two-dimensional ultrasonic receiver array, a light-energy emitter, a display, and a control system. The control system may be configured to determine whether an object is in contact with the display, and upon the determination that an object is contacting the display, may cause the light-energy emitter to emit light-energy at a first wavelength and a first intensity, the first wavelength and the first intensity being sufficient to photoacoustically generate first ultrasonic waves from a first subdermal feature. The control system may further set a first range gate and a first range gate delay for the two-dimensional ultrasonic receiver array corresponding to a depth of the first subdermal feature, and receive, from the two-dimensional ultrasonic receiver array, first signals representing the first ultrasonic waves from the first subdermal feature within the first range gate and may process the second signals representing the second ultrasonic waves into second image data of the second subdermal feature.

In some implementations, a mobile device may be, or may include, the apparatus. For example, a mobile device, such as a phone or a watch, may include a biometric system as disclosed herein.

The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system may be capable of controlling the light-energy emitter to emit light and of receiving signals from the ultrasonic receiver array corresponding to acoustic waves emitted from portions of a target object. The emissions may be due to the target object being illuminated with light emitted by the light-energy emitter.

In some examples, the light-energy emitter may include one or more laser diodes or light-emitting diodes. For example, the light-energy emitter may include at least one infrared, optical, red, green, blue, white or ultraviolet light-emitting diode and/or at least one infrared, optical, red, green, blue or ultraviolet laser diode. In some implementations, the light-energy emitter may be capable of emitting a light pulse with a pulse width less than about 100 nanoseconds. In some examples, the light-energy emitter may be capable of emitting a plurality of light pulses at a pulse frequency between about 1 MHz and about 100 MHz. According to some examples, the control system may be capable of selecting one or more acquisition time delays, or range gate delays (RGD's) to receive acoustic wave emissions from one or more corresponding distances from the ultrasonic receiver array.

In some implementations, the control system may be capable of selecting a wavelength of the light emitted by the light-energy emitter. According to some such implementations, the control system may be capable of selecting the wavelength and a light intensity associated with the selected wavelength to illuminate portions of the target object.

According to some examples, the information obtained from the received image data may include attribute information corresponding to at least one of sub-epidermal features, muscle tissue features or bone tissue features. In some implementations, the information obtained from the received image data and the stored attribute information may include attribute information corresponding to sub-epidermal features. In some such implementations, the sub-epidermal features may include features of the dermis, features of the subcutis, blood vessel features, lymph vessel features, sweat gland features, hair follicle features, hair papilla features and/or fat lobule features.

In some examples, the control system may be capable of obtaining ultrasonic image data via illumination of the target object with light emitted from the light-energy emitter. Alternatively, or additionally, the ultrasonic image data obtained via illumination of the target object may include vascular image data.

According to some implementations, the target object may be positioned on a surface of the ultrasonic receiver array or positioned on a surface of a platen that is acoustically coupled to the ultrasonic receiver array. In some examples, the target object may be a finger or a finger-like object. According to some implementations, the control system may be configured to make a liveness determination of the target object based on the received signals. According to some implementations, there may be a display coupled to the ultrasonic receiver array.

Other innovative aspects of the subject matter described in this disclosure can be implemented in a subdermal imaging method that may involve determining, by a control system, whether an object is in contact with a display, and upon the determination that the object is contacting the display, emitting light-energy, by a light-energy emitter, at a first wavelength and a first intensity, the first wavelength and the first intensity being sufficient to photoacoustically generate first ultrasonic waves from a first subdermal feature. The method may further involve setting a first range gate and a first range gate delay, for a two-dimensional ultrasonic receiver array, corresponding to a depth of the first subdermal feature, and receiving, from the two-dimensional ultrasonic receiver array, first signals representing the first ultrasonic waves from the first subdermal feature within the first range gate; and processing the first signals representing the first ultrasonic waves into first image data of the first subdermal feature.

In some instances, the method may involve selecting a wavelength and a light intensity of the light emitted by the light-energy emitter to selectively generate acoustic wave emissions from portions of the target object. In some examples, the method may involve selecting an acquisition time delay, or range gate delay (RGD) to receive acoustic wave emissions at a corresponding distance from the ultrasonic receiver array.

In some examples, controlling the light-energy emitter may involve controlling a light-energy emitter of a mobile device. In some such examples, controlling the light-energy emitter involves controlling at least one backlight or front light capable of illuminating a display of the mobile device.

Some or all of the methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in a non-transitory medium having software stored thereon.

Other innovative aspects of the subject matter described in this disclosure also can be implemented in an apparatus. The apparatus may include an ultrasonic receiver array, a light-energy emitter, a display, and a control system. In some examples, the apparatus may be, or may include, a subdermal imaging system. In some implementations, a mobile device may be, or may include, the apparatus. For example, a mobile device may include a subdermal imaging system as disclosed herein. In some implementations, the ultrasonic receiver array and a portion of the light-energy emitter may be configured in an ultrasonic button, a display module and/or a mobile device enclosure.

The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system may be operatively configured to control the light-energy emitter to emit light that induces acoustic wave emissions inside a target object. The control system may be operatively configured to select a first acquisition time delay for the reception of acoustic wave emissions primarily from a first depth inside the target object. The control system may be operatively configured to acquire first ultrasonic image data from the acoustic wave emissions received by the ultrasonic receiver array during a first acquisition time window. The first acquisition time window, or range gate, may be initiated at an end time of the first acquisition time delay. In some implementations, the first ultrasonic image data may be acquired during the first acquisition time window from a peak detector circuit disposed in each of a plurality of sensor pixels within the ultrasonic receiver array.

In some examples, the apparatus may include a display. The control system may be configured to control the display to depict a two-dimensional image that corresponds with the first ultrasonic image data.

According to some examples, the acquisition time delay may be measured from a time that the light-energy emitter emits light. In some implementations, the first acquisition time window may be in the range of about 10 nanoseconds to about 200 nanoseconds. In some instances, the control system may be operatively configured to select second through $N^{th}$ acquisition time delays and to acquire second through $N^{th}$ ultrasonic image data during second through $N^{th}$ acquisition time windows after the second through $N^{th}$ acquisition time delays. Each of the second through $N^{th}$ acquisition time delays may correspond to a second through an $N^{th}$ depth inside the target object. In some such examples, the apparatus may include a display and the control system may be configured to control the display to depict a three-dimensional image that corresponds with at least a subset of the first through $N^{th}$ ultrasonic image data.

In some examples, the light-energy emitter may include one or more laser diodes, semiconductor lasers and/or light-emitting diodes. For example, the light-energy emitter may include at least one infrared, optical, red, green, blue, white or ultraviolet light-emitting diode and/or at least one infrared, optical, red, green, blue or ultraviolet laser diode. In some implementations, the light-energy emitter may be capable of emitting a light pulse with a pulse width less than about 100 nanoseconds. According to some implementations, the control system may be configured to control the light-energy emitter to emit at least one light pulse having a duration that is in the range of about 10 nanoseconds to about 500 nanoseconds. In some examples, the light-energy emitter may be capable of emitting a plurality of light pulses at a pulse frequency between about 1 MHz and about 100 MHz.

In some implementations, the apparatus may include a substrate. In some such implementations, the ultrasonic receiver array may be formed in or on the substrate. In some examples, the light-energy emitter may be coupled to the substrate. According to some implementations, the light emitted by the light-energy emitter may be transmitted through the substrate. In some examples, light emitted by the light-energy emitter may be transmitted through the ultrasonic receiver array. In some implementations, the light emitted by the light-energy emitter may include a plurality of light pulses and the pulse frequency of the plurality of light pulses may correspond to an acoustic resonant frequency of the ultrasonic receiver array and/or the substrate. According to some examples, the control system may be capable of selecting one or more acquisition time delays to receive acoustic wave emissions from one or more corresponding distances from the ultrasonic receiver array.

In some implementations, the control system may be capable of selecting a wavelength of the light emitted by the light-energy emitter. According to some such implementations, the control system may be capable of selecting the wavelength and a light intensity associated with the selected wavelength to illuminate portions of the target object. In some examples, the control system may be configured to select one or more wavelengths of the light to trigger acoustic wave emissions primarily from a particular type of material in the target object.

According to some implementations, the target object may be positioned on a surface of the ultrasonic receiver array or positioned on a surface of a platen that is acoustically coupled to the ultrasonic receiver array. In some examples, the target object may be a finger or a finger-like object. According to some implementations, the control system may be configured to make a liveness determination of the target object based on the received signals.

In some examples, the control system may be configured to estimate a blood oxygen level. According to some implementations, the control system may be configured to estimate a blood glucose level. According to some implementations, the control system may be configured to measure vascular characteristics.

In some examples, the acquisition time delay may be measured from a time that the light-energy emitter emits light. In some instances, the first acquisition time window may be in the range of about 10 nanoseconds to about 200 nanoseconds.

In some examples, the method may involve selecting second through $N^{th}$ acquisition time delays and acquiring second through $N^{th}$ ultrasonic image data during second through $N^{th}$ acquisition time windows after the second through $N^{th}$ acquisition time delays. In some such examples, each of the second through $N^{th}$ acquisition time delays may correspond to a second through an $N^{th}$ depth inside the target object.

The first acquisition time window, or range gate may, for example, be initiated at an end time of the first acquisition time delay, or range gate delay. In some examples, the acquisition time delay is measured from a time that the light-energy emitter emits light.

BRIEF DESCRIPTION OF THE DRAWINGS

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale. Like reference numbers and designations in the various drawings indicate like elements.

FIGS. 10D-10F show a series of simplified two-dimensional images and a three-dimensional reconstruction that correspond with ultrasonic image data acquired by the processes shown in FIGS. 10A-10C.

DETAILED DESCRIPTION

Figure 1:
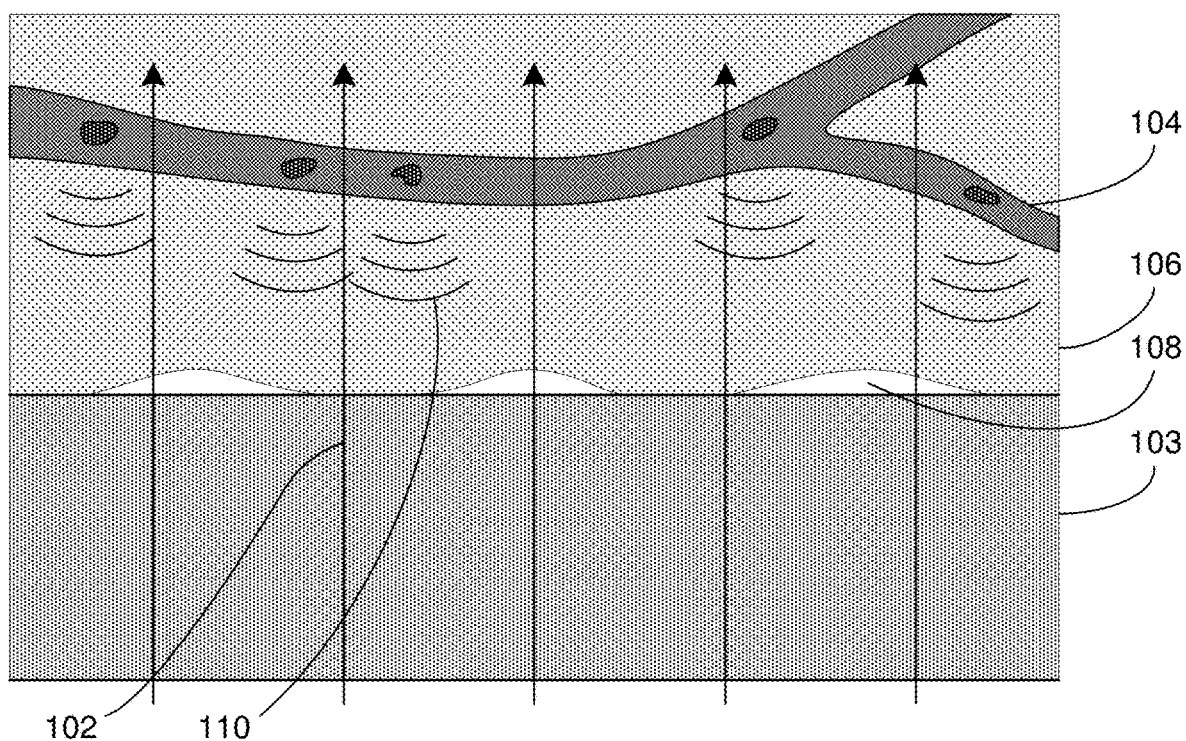
FIG. 1 shows an example of components of blood being differentially heated by incident light and subsequently emitting acoustic waves.

The following description is directed to certain implementations for the purposes of describing the innovative aspects of this disclosure. However, a person having ordinary skill in the art will readily recognize that the teachings herein may be applied in a multitude of different ways. The described implementations may be implemented in any device, apparatus, or system that includes a biometric system as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, hand-held or portable computers, netbooks, notebooks, smartbooks, tablets, printers, copiers, scanners, facsimile devices, global positioning system (GPS) receivers/navigators, cameras, digital media players (such as MP3 players), camcorders, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), electronic photographs, electronic billboards or signs, projectors, architectural structures, microwaves, refrigerators, stereo systems, cassette recorders or players, DVD players, CD players, VCRs, radios, portable memory chips, washers, dryers, washer/dryers, parking meters, packaging (such as in electromechanical systems (EMS) applications including microelectromechanical systems (MEMS) applications, as well as non-EMS applications), aesthetic structures (such as display of images on a piece of jewelry or clothing) and a variety of EMS devices. The teachings herein also may be used in applications such as, but not limited to, electronic switching devices, radio frequency filters, sensors, accelerometers, gyroscopes, motion-sensing devices, magnetometers, inertial components for consumer electronics, parts of consumer electronics products, steering wheels or other automobile parts, varactors, liquid crystal devices, electrophoretic devices, drive schemes, manufacturing processes and electronic test equipment. Thus, the teachings are not intended to be limited to the implementations depicted solely in the Figures, but instead have wide applicability as will be readily apparent to one having ordinary skill in the art.

Various implementations disclosed herein may include a biometric system that is capable of optical excitation and ultrasonic imaging of resultant acoustic wave generation. Such imaging may be referred to herein as "photoacoustic imaging." Some such implementations may be capable of obtaining images from bones, muscle tissue, blood, blood vessels, veins, capillaries, and/or other sub-epidermal features. As used herein, the term "sub-epidermal features" may refer to any of the tissue layers that underlie the epidermis, including the dermis, the subcutis, etc., and any blood vessels, lymph vessels, sweat glands, hair follicles, hair papilla, fat lobules, etc., that may be present within such tissue layers. Some implementations may be capable of biometric authentication that is based, at least in part, on image data obtained via photoacoustic imaging. In some examples, an authentication process may be based on image data obtained via photoacoustic imaging and also on image data obtained by transmitting ultrasonic waves and detecting corresponding reflected ultrasonic waves.

In some implementations, the incident light wavelength or wavelengths emitted by a light-energy emitter may be selected to trigger acoustic wave emissions primarily from a particular type of material, such as blood, blood cells, blood vessels, blood vasculature, lymphatic vasculature, other soft tissue, or bones. The acoustic wave emissions may, in some examples, include ultrasonic waves. In some such implementations, the control system may be capable of estimating a blood oxygen level, estimating a blood glucose level, or estimating both a blood oxygen level and a blood glucose level.

Alternatively, or additionally, the time interval between the irradiation time and the time during which resulting ultrasonic waves are sampled (which may be referred to herein as the acquisition time delay or the range-gate delay (RGD)) may be selected to receive acoustic wave emissions primarily from a particular depth and/or from a particular type of material. For example, a relatively larger range-gate delay may be selected to receive acoustic wave emissions primarily from bones and a relatively smaller range-gate delay may be selected to receive acoustic wave emissions primarily from sub-epidermal features (such as blood vessels, blood, etc.), muscle tissue features or bone tissue features.

Accordingly, some biometric systems disclosed herein may be capable of acquiring images of sub-epidermal features via photoacoustic imaging. In some implementations, a control system may be capable of acquiring first ultrasonic image data from acoustic wave emissions that are received by an ultrasonic receiver array during a first acquisition time window that is initiated at an end time of a first acquisition time delay. According to some examples, the control system may be capable of controlling a display to depict a two-dimensional (2-D) image that corresponds with the first ultrasonic image data. In some instances, the control system may be capable of acquiring second through Nth ultrasonic image data during second through Nth acquisition time windows after second through Nth acquisition time delays. Each of the second through Nth acquisition time delays may correspond to a second through an Nth depth inside the target object. According to some examples, the control system may be capable of controlling a display to depict a three-dimensional (3-D) image that corresponds with at least a subset of the first through Nth ultrasonic image data.

Particular implementations of the subject matter described in this disclosure can be implemented to realize one or more of the following potential advantages. Imaging sub-epidermal features (such as blood vessels, blood, etc.), muscle tissue features, etc., using ultrasonic technology alone can be challenging due to the small acoustic impedance contrast between various types of soft tissue. In some photoacoustic imaging implementations, a relatively higher signal-to-noise ratio may be obtained for the resulting acoustic wave emission detection because the excitation is via optical stimulation instead of (or in addition to) ultrasonic wave transmission. The higher signal-to-noise ratio can provide relatively more accurate and relatively more detailed imaging of blood vessels and other sub-epidermal features. In addition to the inherent value of obtaining more detailed images (e.g., for improved medical determinations and diagnoses), the detailed imaging of blood vessels and other sub-epidermal features can provide more reliable user authentication and liveness determinations. Moreover, some photoacoustic imaging implementations can detect changes in blood oxygen levels, which can provide enhanced liveness determinations. Some implementations provide a mobile device that includes a subdermal imaging system that is capable of some or all of the foregoing functionality. Some such mobile devices may be capable of displaying 2-D and/or 3-D images of sub-epidermal features, bone tissue, etc.

FIG. 1 shows an example of components of blood being differentially heated by incident light and subsequently emitting acoustic waves. In this example, incident light 102 has been transmitted from a light-energy emitter (not shown) through a substrate 103 and into a blood vessel 104 of an overlying finger 106. The surface of the finger 106 includes ridges and valleys, so some of the incident light 102 has been transmitted through the air 108 in this example. Here, the incident light 102 is causing optical excitation of illuminated blood and blood components in the blood vessel 104 and resultant acoustic wave generation. In this example, the generated acoustic waves 110 may include ultrasonic waves.

In some implementations, such acoustic wave emissions may be detected by sensors of a sensor array, such as the ultrasonic receiver array 202 that is described below with reference to FIG. 2. In some instances, the incident light wavelength, wavelengths and/or wavelength range(s) may be selected to trigger acoustic wave emissions primarily from a particular type of material, such as blood, blood components, blood vessels, other soft tissue, or bones.

Figure 2:
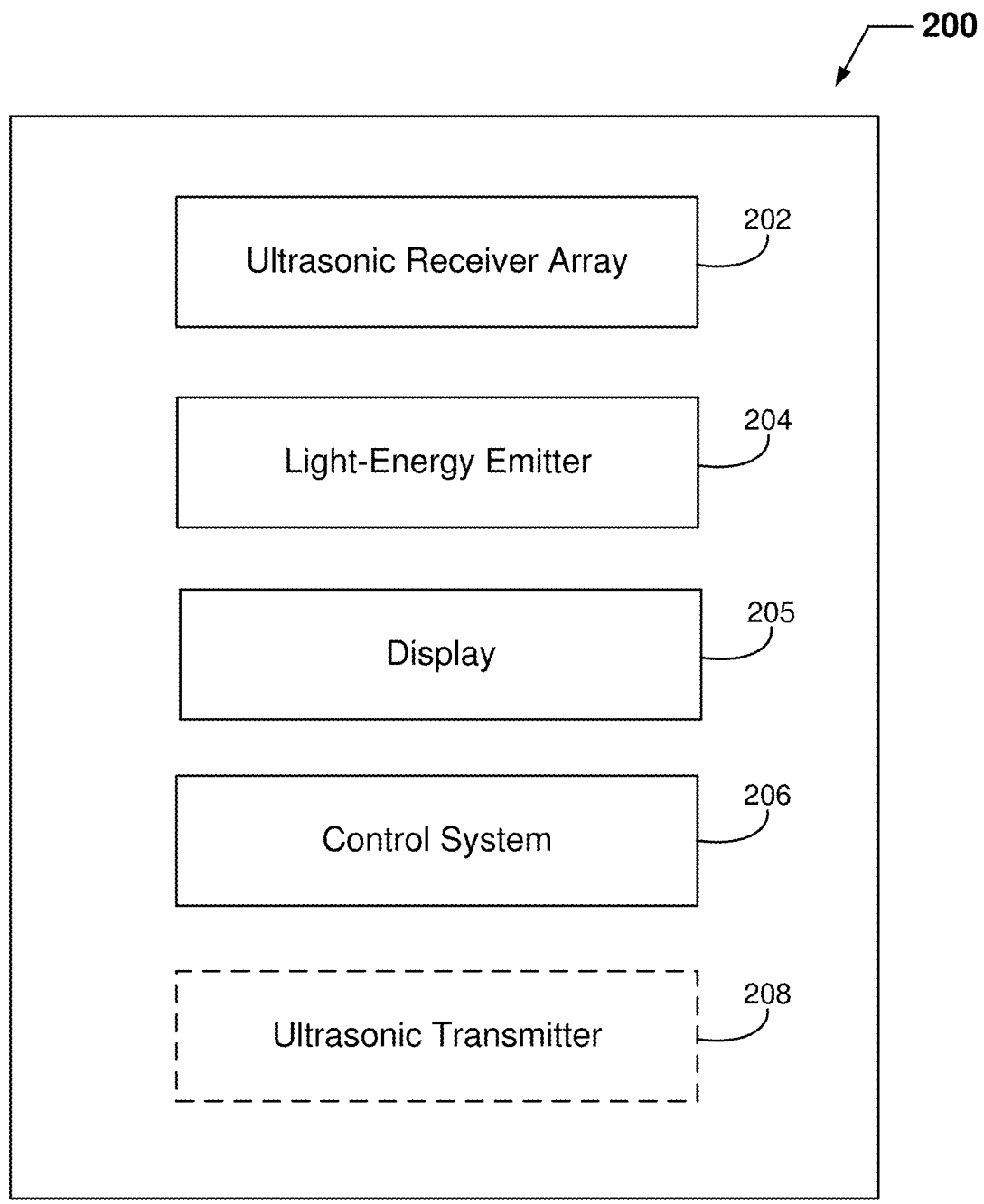
FIG. 2 is a block diagram that shows example components of an apparatus according to some disclosed implementations.

FIG. 2 is a block diagram that shows example components of an apparatus according to some disclosed implementations. In this example, the apparatus 200 includes a biometric system. Here, the biometric system includes an ultrasonic receiver array 202, a light-energy emitter 204, a display 205 and a control system 206. Although not shown in FIG. 2, the apparatus 200 may include a substrate. Some examples are described below. Some implementations of the apparatus 200 may include the optional ultrasonic transmitter 208.

Various examples of ultrasonic receiver arrays 202 are disclosed herein, some of which may include an ultrasonic transmitter and some of which may not. Although shown as separate elements in FIG. 2, in some implementations the ultrasonic receiver array 202 and the ultrasonic transmitter 208 may be combined in an ultrasonic transceiver. For example, in some implementations, the ultrasonic receiver array 202 may include a piezoelectric receiver layer, such as a layer of PVDF polymer or a layer of PVDF-TrFE copolymer. In some implementations, a separate piezoelectric layer may serve as the ultrasonic transmitter. In some implementations, a single piezoelectric layer may serve as the transmitter and as a receiver. In some implementations, other piezoelectric materials may be used in the piezoelectric layer, such as aluminum nitride (AlN) or lead zirconate titanate (PZT). The ultrasonic receiver array 202 may, in some examples, include an array of ultrasonic transducer elements, such as an array of piezoelectric micromachined ultrasonic transducers (PMUTs), an array of capacitive micromachined ultrasonic transducers (CMUTs), etc. In some such examples, a piezoelectric receiver layer, PMUT elements in a single-layer array of PMUTs, or CMUT elements in a single-layer array of CMUTs, may be used as ultrasonic transmitters as well as ultrasonic receivers. According to some alternative examples, the ultrasonic receiver array 202 may be an ultrasonic receiver array and the ultrasonic transmitter 208 may include one or more separate elements. In some such examples, the ultrasonic transmitter 208 may include an ultrasonic plane-wave generator, such as those described below.

The light-energy emitter 204 may, in some examples, include an array of light-emitting diodes. In some implementations, the light-energy emitter 204 may include one or more laser diodes. According to some implementations, the light-energy emitter may include at least one infrared, optical, red, green, blue, white or ultraviolet light-emitting diode. In some implementations, the light-energy emitter 204 may include one or more laser diodes. For example, the light-energy emitter 204 may include at least one infrared, optical, red, green, blue or ultraviolet laser diode.

The display 205 may be any one of an LED, TFT, OLED, or other type of display capable of displaying visual information. The light emitted from the light-energy emitter 204 may be transmitted through the display 205 to trigger acoustic wave emissions in a material proximate the display. In some implementations, the light-energy emitter 204 may be collocated with the display 205. For example, the light-energy emitter 204 may be pixels located proximate RGB pixels of a display 205.

In some implementations, the light-energy emitter 204 may be capable of emitting various wavelengths of light, which may be selectable to trigger acoustic wave emissions primarily from a particular type of material. For example, because the hemoglobin in blood absorbs near-infrared light very strongly, in some implementations the light-energy emitter 204 may be capable of emitting one or more wavelengths of light in the near-infrared range, in order to trigger acoustic wave emissions from hemoglobin. However, in some examples the control system 206 may control the wavelength(s) of light emitted by the light-energy emitter 204 to preferentially induce acoustic waves in blood vessels, other soft tissue, and/or bones. For example, an infrared (IR) light-emitting diode LED may be selected and a short pulse of IR light emitted to illuminate a portion of a target object and generate acoustic wave emissions that are then detected by the ultrasonic receiver array 202. In another example, an IR LED and a red LED or other color such as green, blue, white or ultraviolet (UV) may be selected and a short pulse of light emitted from each light source in turn with ultrasonic images obtained after light has been emitted from each light source. In other implementations, one or more light sources of different wavelengths may be fired in turn or simultaneously to generate acoustic emissions that may be detected by the ultrasonic receiver array. Image data from the ultrasonic receiver array that is obtained with light sources of different wavelengths and at different depths (e.g., varying RGDs) into the target object may be combined to determine the location and type of material in the target object. Image contrast may occur as materials in the body generally absorb light at different wavelengths differently. As materials in the body absorb light at a specific wavelength, they may heat differentially and generate acoustic wave emissions with sufficiently short pulses of light having sufficient intensities. Depth contrast may be obtained with light of different wavelengths and/or intensities at each selected wavelength. That is, successive images may be obtained at a fixed RGD (which may correspond with a fixed depth into the target object) with varying light intensities and wavelengths to detect materials and their locations within a target object.

For example, hemoglobin, blood glucose or blood oxygen within a blood vessel inside a target object such as a finger may be detected photoacoustically.

According to some implementations, the control system 206 may be configured to analyze first image data to determine a first metric. Such a metric may be an indication of image quality, a depth of a subdermal feature, an indication of image intensity, or any other metric determined by an analysis of the first image data.

In an implementation, the control system 206 may be configured to set a second range gate and second range gate delay for the two-dimensional ultrasonic receiver array at least in part on the basis of the first metric. For example, the first metric may indicate that a deeper or shallower subdermal feature should be analyzed, or a first metric indicates that the light wavelength and intensity is not sufficient to provide a suitable image, and therefore the wavelength and intensity should be modified, which involves emitting, with the light-energy emitter, light energy at a second wavelength and a second intensity, the second wavelength and the second intensity being sufficient to photoacoustically generate second ultrasonic waves from a second subdermal feature. The control system 206 may also be configured to receive, from the two-dimensional ultrasonic receiver array, second signals representing the second ultrasonic waves from the second subdermal feature within the second range gate. The control system 206 may be further configured to process the second signals representing the second ultrasonic waves into second image data of the second subdermal feature. These second signals, emitted photoacoustically from subdermal features excited via the second wavelength and/or second intensity, may, when processed, provide an image with different characteristics from the first image. For example, a second wavelength or intensity may provide a clearer image of blood vessels or capillaries at a second depth. Additionally, the second range gate and second range gate delay may allow the ultrasonic receiver array 202 to properly acquire the signals at the second depth.

The control system may be further configured to receive an input from a first sensor, the first sensor being different from the two-dimensional ultrasonic receiver array. This sensor may be an optical sensor, a temperature sensor, a moisture sensor, a capacitive sensor, a pressure sensor, or any type of sensor that transduces physical measurements into electrical signals or characteristics that may be measured through electrical processes. On the basis of the sensor input, the control system may be configured to set a second range gate delay and range gate in order to receive, with the ultrasonic receiver array 202, signals from a second depth. For example, the sensor output may indicate that a deeper or shallower subdermal feature should be analyzed, or a first metric indicates that the light wavelength and intensity is not sufficient to provide a suitable image, and therefore the wavelength and intensity should be modified, which involves emitting, with the light-energy emitter, light energy at a second wavelength and a second intensity, the second wavelength and the second intensity being sufficient to photoacoustically generate second ultrasonic waves from a second subdermal feature. The control system 206 may also be configured to receive, from the two-dimensional ultrasonic receiver array, second signals representing the second ultrasonic waves from the second subdermal feature within the second range gate. The control system 206 may be further configured to process the second signals representing the second ultrasonic waves into second image data of the second subdermal feature. These second signals, emitted photoacoustically from subdermal features excited via the second wavelength and/or second intensity, may, when processed, provide an image with different characteristics from the first image. For example, a second wavelength or intensity may provide a clearer image of blood vessels or capillaries at a second depth. Additionally, the second range gate and second range gate delay may allow the ultrasonic receiver array 202 to properly acquire the signals at the second depth.

The control system 206 may be further configured to determine a first distance to a first subdermal feature, such as a blood vessel, at least in part on the basis of the range gate delay. For example, the range gate delay multiplied by the speed of sound in the mediums through which the ultrasound wave travels would indicate the distance to the subdermal feature. The control system 206 may also be configured to determine a second distance to a second subdermal feature using the aforementioned method. On the basis of the first and second distance, the control system 206 may be further configured to determine a third distance between the two subdermal features. For example, by measuring the distance to one side of a vein, and the distance to the other side of a vein, it may be possible to calculate the distance between the two sides of the vein, and hence the volume of the vein.

According to some implementations, the light-energy emitter 204 may be capable of emitting a light pulse with a pulse width less than about 100 nanoseconds. In some implementations, the light pulse may have a pulse width between about 10 nanoseconds and about 500 nanoseconds or more. In some implementations, the light-energy emitter 204 may be capable of emitting a plurality of light pulses at a pulse frequency between about 1 MHz and about 100 MHz. In some examples, the pulse frequency of the light pulses may correspond to an acoustic resonant frequency of the ultrasonic receiver array and the substrate. For example, a set of four or more light pulses may be emitted from the light-energy emitter 204 at a frequency that corresponds with the resonant frequency of a resonant acoustic cavity in the sensor stack, allowing a build-up of the received ultrasonic waves and a higher resultant signal strength. In some implementations, filtered light or light sources with specific wavelengths for detecting selected materials may be included with the light-energy emitter 204. In some implementations, the light-energy emitter may contain light sources such as red, green and blue LEDs of a display that may be augmented with light sources of other wavelengths (such as IR and/or UV) and with light sources of higher optical power. For example, high-power laser diodes or electronic flash units (e.g., an LED or xenon flash unit) with or without filters may be used for short-term illumination of the target object.

The control system 206 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 206 also may include (and/or be configured for communication with) one or more memory devices, such as one or more random access memory (RAM) devices, read-only memory (ROM) devices, etc. Accordingly, the apparatus 200 may have a memory system that includes one or more memory devices, though the memory system is not shown in FIG. 2. The control system 206 may be capable of receiving and processing data from the ultrasonic receiver array 202, e.g., as described below. If the apparatus 200 includes an ultrasonic transmitter 208, the control system 206 may be capable of controlling the ultrasonic transmitter 208, e.g., as disclosed elsewhere herein. In some implementations, functionality of the control system 206 may be partitioned between one or more controllers or processors, such as a dedicated sensor controller and an applications processor of a mobile device.

Although not shown in FIG. 2, some implementations of the apparatus 200 may include an interface system. In some examples, the interface system may include a wireless interface system. In some implementations, the interface system may include a user interface system, one or more network interfaces, one or more interfaces between the control system 206 and a memory system and/or one or more interfaces between the control system 206 and one or more external device interfaces (e.g., ports or applications processors).

The apparatus 200 may be used in a variety of different contexts, many examples of which are disclosed herein. For example, in some implementations a mobile device may include the apparatus 200. In some implementations, a wearable device may include the apparatus 200. The wearable device may, for example, be a bracelet, an armband, a wristband, a ring, a headband or a patch.

Figure 3:
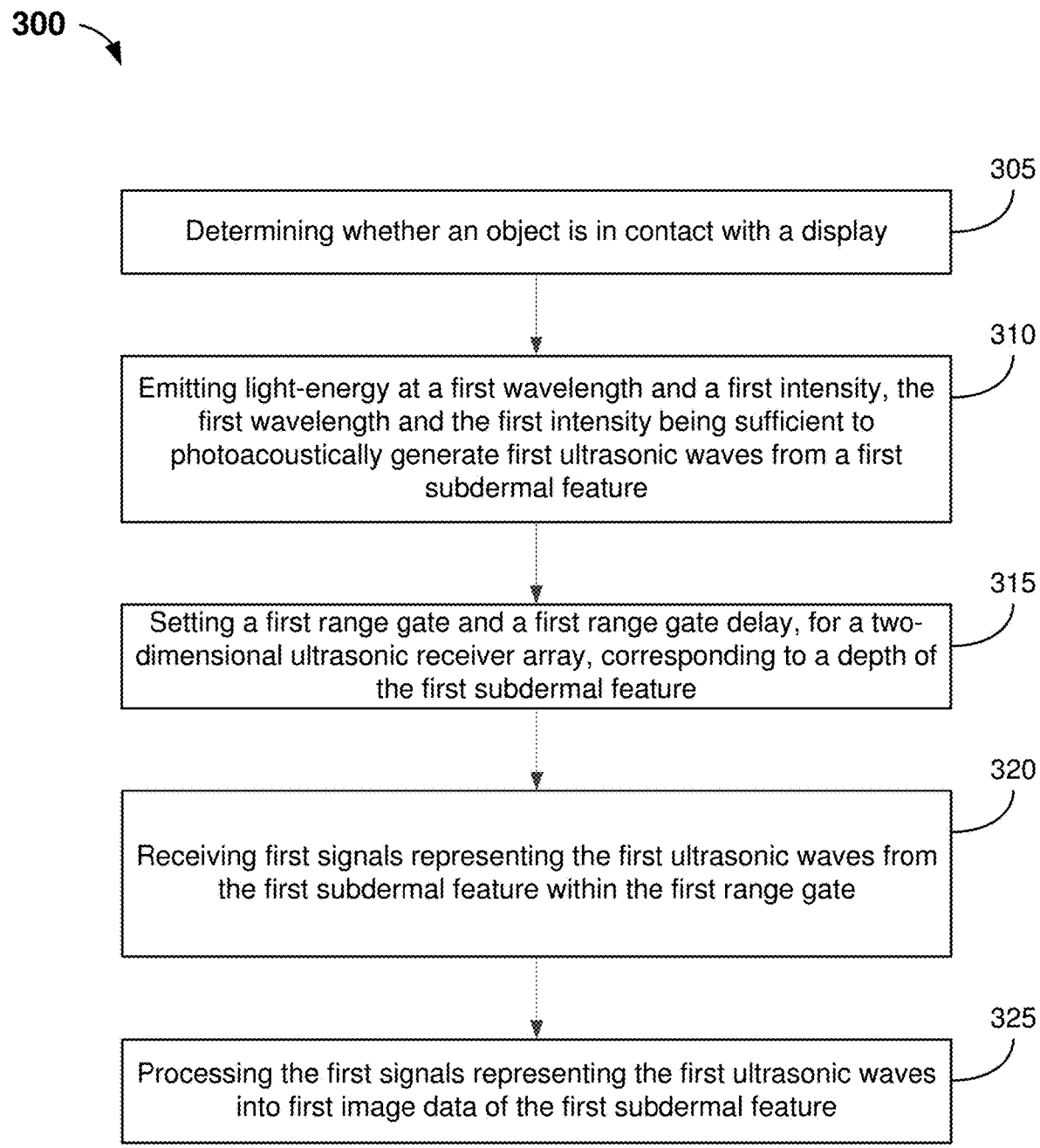
FIG. 3 is a flow diagram that provides examples of a subdermal imaging system operations.

FIG. 3 is a flow diagram of process 300 that provides examples of subdermal imaging system operations. The blocks of FIG. 3 (and those of other flow diagrams provided herein) may, for example, be performed by the apparatus 200 of FIG. 2 or by a similar apparatus. As with other methods disclosed herein, the method outlined in FIG. 3 may include more or fewer blocks than indicated. Moreover, the blocks of methods disclosed herein are not necessarily performed in the order indicated.

Here, block 305 involves determining whether an object is in contact with a display. In some implementations, the control system 206 of the apparatus 200 may perform the determination of whether an object is in contact with a display. In some examples, the control system 206 may use a capacitance measurement to determine whether an object is in contact with a display. In other examples, the control system 206 may use a resistive, optical, or ultrasound measurement to determine whether an object is in contact with a display.

Block 310 involves emitting light-energy at a first wavelength and a first intensity, the first wavelength and the first intensity being sufficient to photoacoustically generate first ultrasonic waves from a first subdermal feature. In some implementations, the control system 206 of the apparatus 200 may control the light-energy emitter 204 to emit light. According to some such implementations, the control system may be capable of selecting one or more wavelengths of the light emitted by the light-energy emitter. In some implementations, the control system may be capable of selecting a light intensity associated with each selected wavelength. For example, the control system may be capable of selecting the one or more wavelengths of light and light intensities associated with each selected wavelength to generate acoustic wave emissions from one or more portions of the target object. In some examples, the control system may be capable of selecting the one or more wavelengths of light to evaluate a one or more characteristics of the target object, e.g., to evaluate blood oxygen levels. Some examples are described below. In some examples, block 310 may involve controlling a light-energy emitter to emit light that is transmitted through a substrate and/or other layers of an apparatus such as the apparatus 200.

Block 315 involves setting a first range gate and a first range gate delay, for a two-dimensional ultrasonic receiver array, corresponding to a depth of the first subdermal feature. In some examples, the control system may be capable of selecting an acquisition time delay, or range gate delay, to receive acoustic wave emissions at a corresponding distance from the ultrasonic receiver array. The corresponding distance may correspond to a depth of a subdermal feature within the target object. According to some examples, the control system may be capable of receiving an acquisition time delay via a user interface, from a data structure stored in memory, etc.

According to some implementations, block 320 involves receiving first signals representing the first ultrasonic waves from the first subdermal feature within the first range gate. In some instances the target object may be positioned on a surface of the ultrasonic receiver array or positioned on a surface of a platen that is acoustically coupled to the ultrasonic receiver array such as a display 205 or cover glass. The ultrasonic receiver array may, in some implementations, be the ultrasonic receiver array 202 that is shown in FIG. 2 and described above. One or more coatings or acoustic matching layers may be included with the platen.

Block 325 involves processing the first signals representing the first ultrasonic waves into first image data of the first subdermal feature. In some examples, such processing may involve displaying, on a display 205, at least a portion of the image data, or an analysis of the image data.

In some examples the target object may be a finger, as shown above in FIG. 1 and as described below with reference to FIG. 4. However, in other examples the target object may be another body part, such as a palm, a wrist, an arm, a leg, a torso, a head, etc.

In some implementations, the control system may be capable of acquiring first ultrasonic image data from acoustic wave emissions that are received by an ultrasonic receiver array during a first acquisition time window that is initiated at an end time of a first acquisition time delay. According to some examples, the control system may be capable of controlling a display to depict a two-dimensional (2-D) image that corresponds with the first image data. In some instances, the control system may be capable of acquiring second through Nth ultrasonic image data during second through Nth acquisition time windows after second through Nth acquisition time delays. Each of the second through Nth acquisition time delays may correspond to second through Nth depths inside the target object. According to some examples, the control system may be capable of controlling a display to depict a reconstructed three-dimensional (3-D) image that corresponds with at least a subset of the first through Nth ultrasonic image data. Some examples are described below.

In some such examples, the ultrasonic image data obtained via illumination of the target object may include image data corresponding to one or more sub-epidermal features, such as vascular image data. In some examples, the attribute information obtained from received image data and the stored attribute information include attribute information regarding subdermal features. According to some such examples, the attribute information may include information regarding subdermal features, such as information regarding features of the dermis, features of the subcutis, blood vessel features, lymph vessel features, sweat gland features, hair follicle features, hair papilla features and/or fat lobule features.

Alternatively, or additionally, in some implementations the attribute information obtained from the received image data and the stored attribute information may include information regarding bone tissue features, muscle tissue features and/or epidermal tissue features.

Similarly, attribute information corresponding to subdermal features may include information regarding the attributes of blood vessels, such as information regarding the types and locations of blood vessel features, such as blood vessel size, blood vessel orientation, the locations of blood vessel branch points, etc. Alternatively, or additionally, biometric data corresponding to subdermal features may include attribute information regarding the types (e.g., the sizes, shapes, orientations, etc.) and locations of features of the dermis, features of the subcutis, lymph vessel features, sweat gland features, hair follicle features, hair papilla features and/or fat lobule features.

Figure 4:
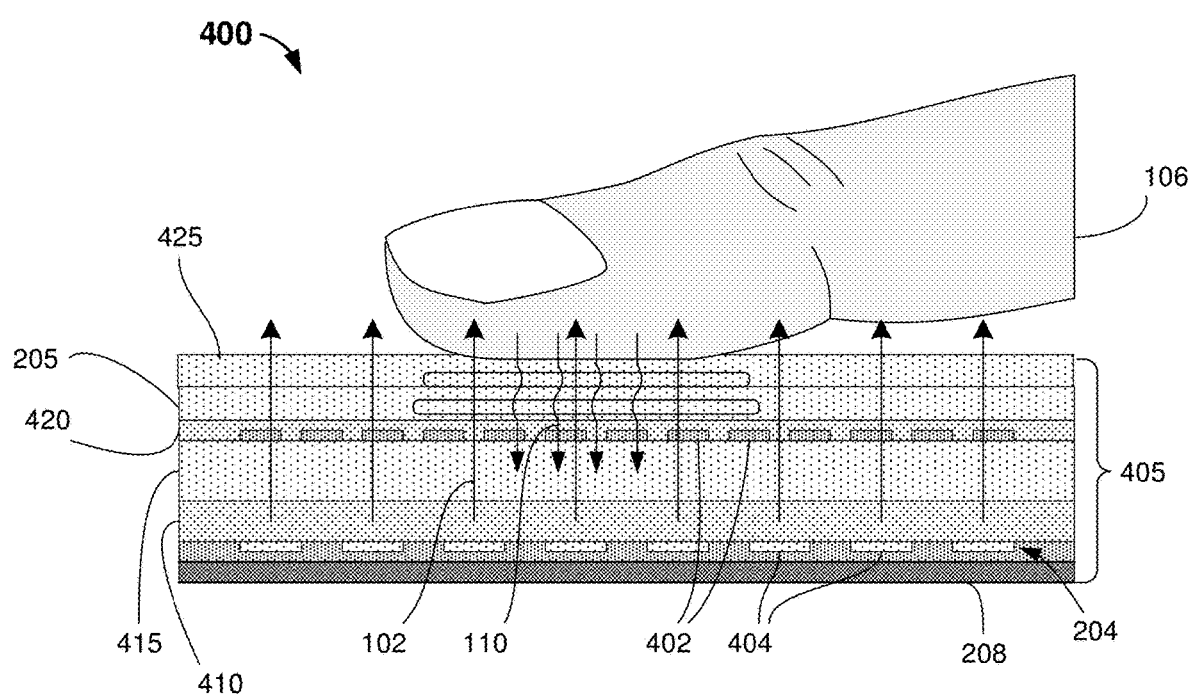
FIG. 4 shows an example of a cross-sectional view of an apparatus capable of performing the method of FIG. 3.

FIG. 4 shows an example of a cross-sectional view of an apparatus capable of performing the method of FIG. 3. The apparatus 400 is an example of a device that may be included in a subdermal imaging system such as those disclosed herein. Here, the apparatus 400 is an implementation of the apparatus 200 that is described above with reference to FIG. 2. As with other implementations shown and described herein, the types of elements, the arrangement of the elements and the dimensions of the elements illustrated in FIG. 4 are merely shown by way of example.

FIG. 4 shows an example of a target object being illuminated by incident light and subsequently emitting acoustic waves. In this example, the apparatus 400 includes a light-energy emitter 204, which may include an array of light-emitting diodes and/or an array of laser diodes. In some implementations, the light-energy emitter 204 may be capable of emitting various wavelengths of light, which may be selectable to trigger acoustic wave emissions primarily from a particular type of material. In some instances, the incident light wavelength, wavelengths and/or wavelength range(s) may be selected to trigger acoustic wave emissions primarily from a particular type of material, such as blood, blood vessels, other soft tissue, or bones. To achieve sufficient image contrast, light sources 404 of the light-energy emitter 204 may need to have a higher intensity and optical power output than light sources generally used to illuminate displays. In some implementations, light sources with light output of 1-100 millijoules or more per pulse, with pulse widths of 100 nanoseconds or less, may be suitable. In some implementations, light from an electronic flash unit such as that associated with a mobile device may be suitable. In some implementations, the pulse width of the emitted light may be between about 10 nanoseconds and about 500 nanoseconds or more.

In this example, incident light 102 has been transmitted from the light sources 404 of the light system 204 through a sensor stack 405 and the display 205, and into an overlying finger 106. The various layers of the sensor stack 405 may include one or more substrates of glass or other material such as plastic or sapphire that is substantially transparent to the light emitted by the light-energy emitter 204. In this example, the sensor stack 405 includes a substrate 410 to which the light-energy emitter 204 is coupled, which may be a backlight of a display according to some implementations. In alternative implementations, the light-energy emitter 204 may be coupled to a front light. Accordingly, in some implementations the light-energy emitter 204 may be configured for illuminating a display and the target object. In some implementations, the light-energy emitter 204 may be collocated with the display 205. For example, the light-energy emitter 204 may be one or more pixels located proximate RGB pixels of a display 205.

In this implementation, the substrate 410 is coupled to a thin-film transistor (TFT) substrate 415 for the ultrasonic receiver array 202. According to this example, a piezoelectric receiver layer 420 overlies the sensor pixels 402 of the ultrasonic receiver array 202 and a platen 425 overlies the piezoelectric receiver layer 420. Accordingly, in this example the apparatus 400 is capable of transmitting the incident light 102 through one or more substrates of the sensor stack 405 that include the ultrasonic receiver array 202 with substrate 415 and the platen 425 that may also be viewed as a substrate. In some implementations, sensor pixels 402 of the ultrasonic receiver array 202 may be transparent, partially transparent or substantially transparent, such that the apparatus 400 may be capable of transmitting the incident light 102 through elements of the ultrasonic receiver array 202. In some implementations, the ultrasonic receiver array 202 and associated circuitry may be formed on or in a glass, plastic or silicon substrate.

In this example, the portion of the apparatus 400 that is shown in FIG. 4 includes an ultrasonic receiver array 202 that is capable of functioning as an ultrasonic receiver. According to some implementations, the apparatus 400 may include an ultrasonic transmitter 208. The ultrasonic transmitter 208 may or may not be part of the ultrasonic receiver array 202, depending on the particular implementation. In some examples, the ultrasonic receiver array 202 may include PMUT or CMUT elements that are capable of transmitting and receiving ultrasonic waves, and the piezoelectric receiver layer 420 may be replaced with an acoustic coupling layer. In some examples, the ultrasonic receiver array 202 may include an array of pixel input electrodes and sensor pixels formed in part from TFT circuitry, an overlying piezoelectric receiver layer 420 of piezoelectric material such as PVDF or PVDF-TrFE, and an upper electrode layer positioned on the piezoelectric receiver layer sometimes referred to as a receiver bias electrode. In the example shown in FIG. 4, at least a portion of the apparatus 400 includes an ultrasonic transmitter 208 that can function as a plane-wave ultrasonic transmitter. The ultrasonic transmitter 208 may include a piezoelectric transmitter layer with transmitter excitation electrodes disposed on each side of the piezoelectric transmitter layer.

Here, the incident light 102 causes optical excitation within the finger 106 and resultant acoustic wave generation. In this example, the generated acoustic waves 110 include ultrasonic waves. Acoustic emissions generated by the absorption of incident light may be detected by the ultrasonic receiver array 202. A high signal-to-noise ratio may be obtained because the resulting ultrasonic waves are caused by optical stimulation instead of by reflection of transmitted ultrasonic waves.

Figure 5:
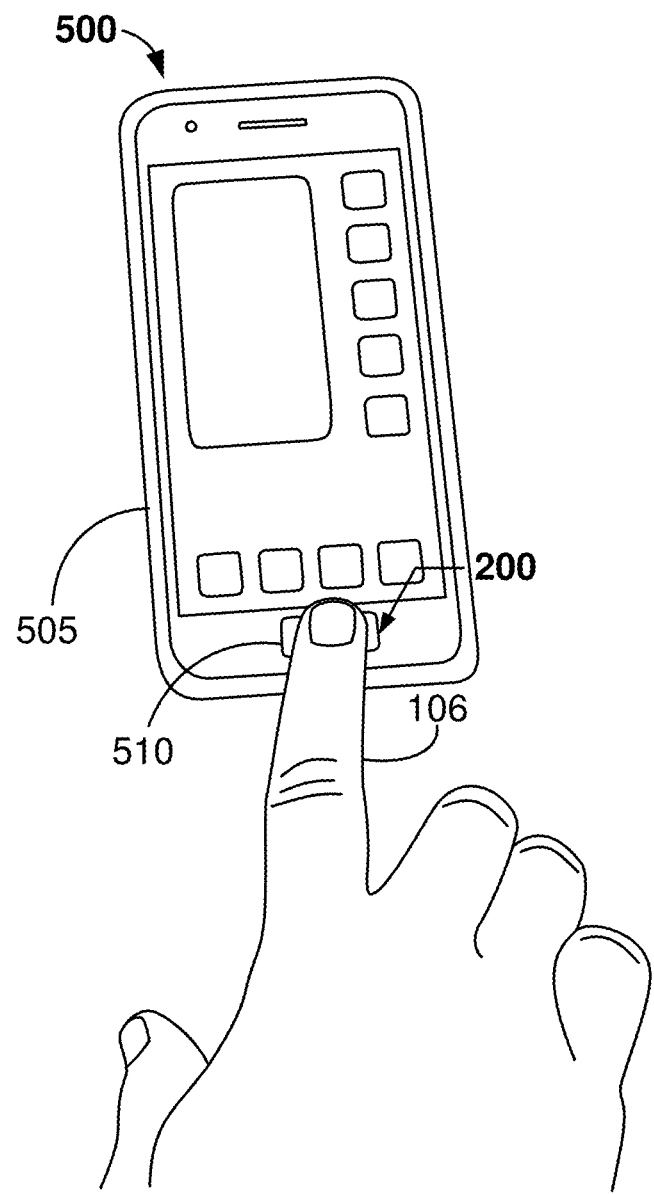
FIG. 5 shows an example of a mobile device that includes a subdermal imaging system as disclosed herein.

FIG. 5 shows an example of a mobile device that includes a biometric system as disclosed herein. In this example, the mobile device 500 is a smart phone. However, in alternative examples the mobile device 500 may another type of mobile device, such as a mobile health device, a wearable device, a tablet, etc.

In this example, the mobile device 500 includes an instance of the apparatus 200 that is described above with reference to FIG. 2. In this example, the apparatus 200 is disposed, at least in part, within the mobile device enclosure 505. According to this example, at least a portion of the apparatus 200 is located in the portion of the mobile device 500 that is shown being touched by the finger 106, which corresponds to the location of button 510. Button 510 may be a physical or a virtual button. Accordingly, the button 510 may be an ultrasonic button. In some implementations, the button 510 may serve as a home button. In some implementations, the button 510 may serve as an ultrasonic authenticating button, with the ability to turn on or otherwise wake up the mobile device 500 when touched or pressed and/or to authenticate or otherwise validate a user when applications running on the mobile device (such as a wake-up function) warrant such a function. Light sources for photoacoustic imaging may be included within the button 510.

In this implementation, the mobile device 500 may be capable of performing a subdermal imaging process. For example, attribute information obtained from the received image data may include attribute information corresponding to at least one of sub-epidermal features, muscle tissue features or bone tissue features.

In some such implementations, the user authentication process may involve evaluating information regarding the fingerprint minutia as well as at least one other type of attribute information, such as attribute information corresponding to subdermal features. According to some such examples, the user authentication process may involve evaluating information regarding the fingerprint minutia as well as attribute information corresponding to vascular features. For example, attribute information obtained from a received image of blood vessels in the finger may be compared with a stored image of blood vessels in the user's finger 106.

The apparatus 200 that is included in the mobile device 500 may or may not include an ultrasonic transmitter, depending on the particular implementation. However, in some examples, the user authentication process may involve obtaining ultrasonic image data via insonification of the target object with ultrasonic waves from an ultrasonic transmitter, as well as obtaining ultrasonic image data via illumination of the target object with light emitted from the light-energy emitter. According to some such examples, the ultrasonic image data obtained via insonification of the target object may include fingerprint image data and the ultrasonic image data obtained via illumination of the target object may include vascular image data.

Figure 6:
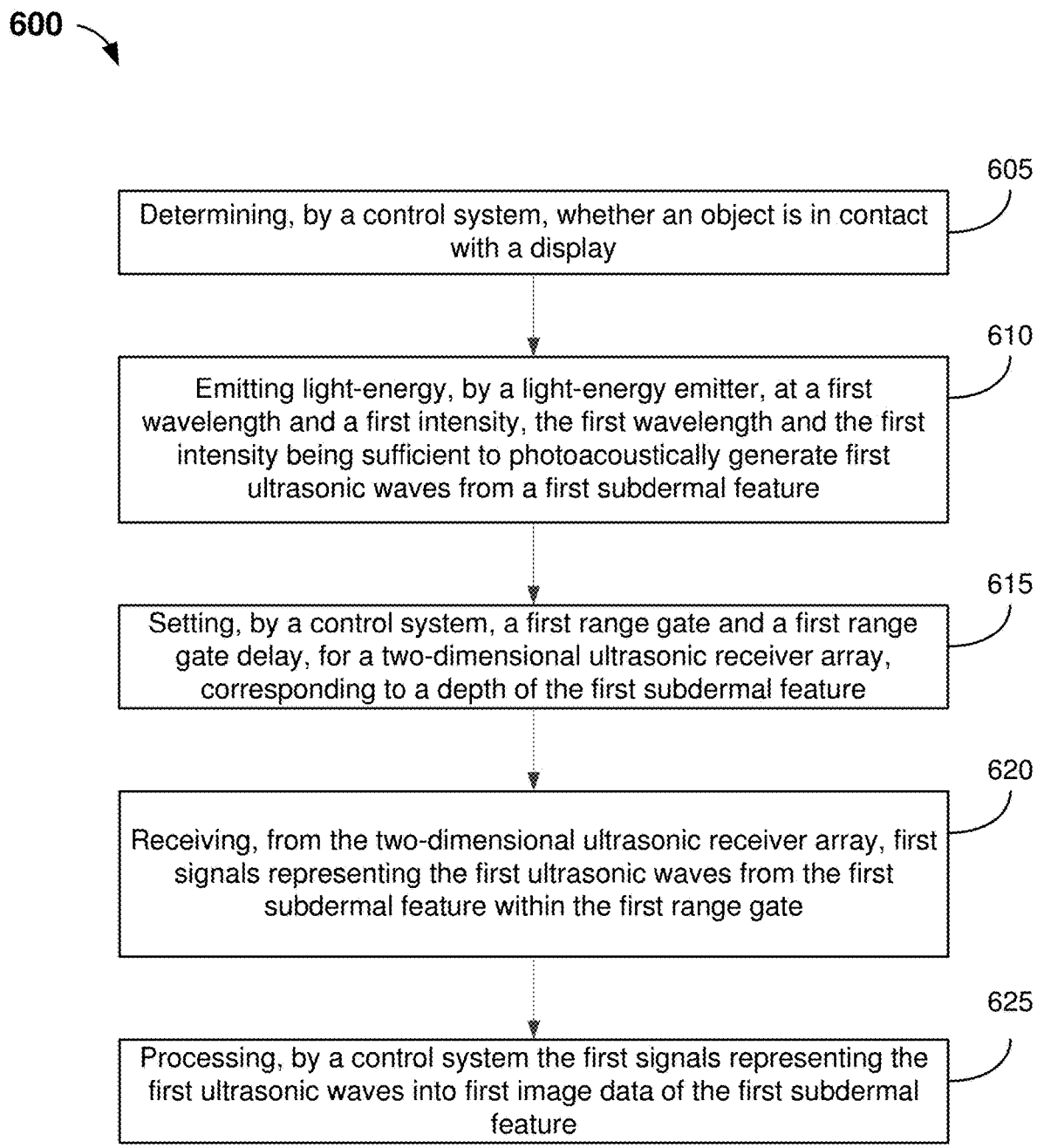
FIG. 6 is a flow diagram that provides further examples of subdermal imaging system operations.

FIG. 6 is a flow diagram that provides further examples of a subdermal imaging system operations. Here, block 605 involves determining whether an object is in contact with a display. In some implementations, the control system 206 of the apparatus 200 may perform the determination of whether an object is in contact with a display. In some examples, the control system 206 may use a capacitance measurement to determine whether an object is in contact with a display. In other examples, the control system 206 may use a resistive, optical, or ultrasound measurement to determine whether an object is in contact with a display. The blocks of FIG. 6 (and those of other flow diagrams provided herein) may, for example, be performed by the apparatus 200 of FIG. 2 or by a similar apparatus. As with other methods disclosed herein, the method outlined in FIG. 6 may include more or fewer blocks than indicated. Moreover, the blocks of method 600, as well as other methods disclosed herein, are not necessarily performed in the order indicated.

Block 610 involves emitting light-energy, by a light-energy emitter, at a first wavelength and a first intensity, the first wavelength and the first intensity being sufficient to photoacoustically generate first ultrasonic waves from a first subdermal feature. In some implementations, the control system 206 of the apparatus 200 may control the light-energy emitter 204 to emit light. According to some such implementations, the control system may be capable of selecting one or more wavelengths of the light emitted by the light-energy emitter. In some implementations, the control system may be capable of selecting a light intensity associated with each selected wavelength. For example, the control system may be capable of selecting the one or more wavelengths of light and light intensities associated with each selected wavelength to generate acoustic wave emissions from one or more portions of the target object. In some examples, the control system may be capable of selecting the one or more wavelengths of light to evaluate a one or more characteristics of the target object, e.g., to evaluate blood oxygen levels. Some examples are described below. In some examples, block 610 may involve controlling a light-energy emitter to emit light that is transmitted through a substrate and/or other layers of an apparatus such as the apparatus 200.

Block 615 involves setting a first range gate and a first range gate delay, for a two-dimensional ultrasonic receiver array, corresponding to a depth of the first subdermal feature. In some examples, the control system may be capable of selecting an acquisition time delay, or range gate delay, to receive acoustic wave emissions at a corresponding distance from the ultrasonic receiver array. The corresponding distance may correspond to a depth of a subdermal feature within the target object. According to some examples, the control system may be capable of receiving an acquisition time delay via a user interface, from a data structure stored in memory, etc.

According to some implementations, block 620 involves receiving, from the two-dimensional ultrasonic receiver array, first signals representing the first ultrasonic waves from the first subdermal feature within the first range gate. In some instances the target object may be positioned on a surface of the ultrasonic receiver array or positioned on a surface of a platen that is acoustically coupled to the ultrasonic receiver array such as a display 205 or cover glass. The ultrasonic receiver array may, in some implementations, be the ultrasonic receiver array 202 that is shown in FIG. 2 and described above. One or more coatings or acoustic matching layers may be included with the platen.

Block 625 involves processing the first signals representing the first ultrasonic waves into first image data of the first subdermal feature. In some examples, such processing may involve displaying, on a display 205, at least a portion of the image data, or an analysis of the image data.

In some examples the target object may be a finger, as shown above in FIG. 1 and as described below with reference to FIG. 4. However, in other examples the target object may be another body part, such as a palm, a wrist, an arm, a leg, a torso, a head, etc.

In some implementations, the control system may be capable of acquiring first ultrasonic image data from acoustic wave emissions that are received by an ultrasonic receiver array during a first acquisition time window that is initiated at an end time of a first acquisition time delay. According to some examples, the control system may be capable of controlling a display to depict a two-dimensional (2-D) image that corresponds with the first image data. In some instances, the control system may be capable of acquiring second through Nth ultrasonic image data during second through Nth acquisition time windows after second through Nth acquisition time delays. Each of the second through Nth acquisition time delays may correspond to second through Nth depths inside the target object. According to some examples, the control system may be capable of controlling a display to depict a reconstructed three-dimensional (3-D) image that corresponds with at least a subset of the first through Nth ultrasonic image data. Some examples are described below.

In some such examples, the ultrasonic image data obtained via illumination of the target object may include image data corresponding to one or more sub-epidermal features, such as vascular image data. In some examples, the attribute information obtained from received image data and the stored attribute information include attribute information regarding subdermal features. According to some such examples, the attribute information may include information regarding subdermal features, such as information regarding features of the dermis, features of the subcutis, blood vessel features, lymph vessel features, sweat gland features, hair follicle features, hair papilla features and/or fat lobule features.

Alternatively, or additionally, in some implementations the attribute information obtained from the received image data and the stored attribute information may include information regarding bone tissue features, muscle tissue features and/or epidermal tissue features.

Similarly, attribute information corresponding to subdermal features may include information regarding the attributes of blood vessels, such as information regarding the types and locations of blood vessel features, such as blood vessel size, blood vessel orientation, the locations of blood vessel branch points, etc. Alternatively, or additionally, biometric data corresponding to subdermal features may include attribute information regarding the types (e.g., the sizes, shapes, orientations, etc.) and locations of features of the dermis, features of the subcutis, lymph vessel features, sweat gland features, hair follicle features, hair papilla features and/or fat lobule features.

According to some exemplary implementations, the control system 206 may be capable of controlling the light-energy emitter 204 to emit at least one light pulse having a duration that is in the range of about 10 nanoseconds to about 500 nanoseconds or more. For example, the control system 206 may be capable of controlling the light-energy emitter 204 to emit at least one light pulse having a duration of approximately 10 nanoseconds, 20 nanoseconds, 30 nanoseconds, 40 nanoseconds, 50 nanoseconds, 60 nanoseconds, 70 nanoseconds, 80 nanoseconds, 90 nanoseconds, 100 nanoseconds, 120 nanoseconds, 140 nanoseconds, 150 nanoseconds, 160 nanoseconds, 180 nanoseconds, 200 nanoseconds, 300 nanoseconds, 400 nanoseconds, 500 nanoseconds, etc. In some such implementations, the control system 206 may be capable of controlling the light-energy emitter 204 to emit a plurality of light pulses at a frequency between about 1 MHz and about 100 MHz. In other words, regardless of the wavelength(s) of light being emitted by the light-energy emitter 204, the intervals between light pulses may correspond to a frequency between about 1 MHz and about 100 MHz or more. For example, the control system 206 may be capable of controlling the light-energy emitter 204 to emit a plurality of light pulses at a frequency of about 1 MHz, about 5 MHz, about 10 MHz, about 15 MHz, about 20 MHz, about 25 MHz, about 30 MHz, about 40 MHz, about 50 MHz, about 60 MHz, about 70 MHz, about 80 MHz, about 90 MHz, about 100 MHz, etc. In some examples, light emitted by the light-energy emitter 204 may be transmitted through an ultrasonic receiver array or through one or more substrates of a sensor stack that includes an ultrasonic receiver array.

Figure 7:
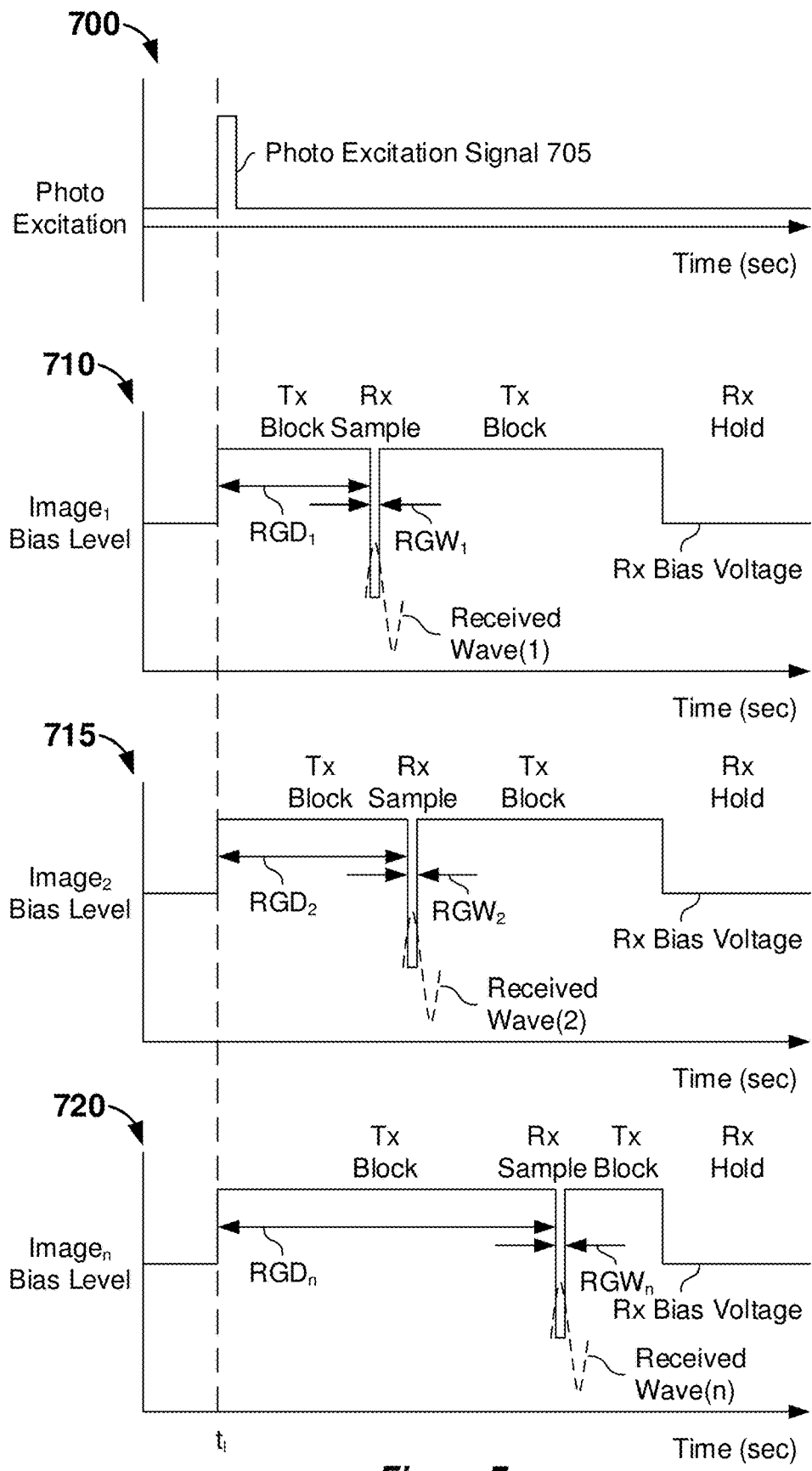
FIG. 7 shows examples of multiple acquisition time delays being selected to receive acoustic waves emitted from different depths.

FIG. 7 shows examples of multiple acquisition time delays being selected to receive acoustic waves emitted from different depths. In these examples, each of the acquisition time delays (which are labeled range-gate delays or RGDs in FIG. 7) is measured from the beginning time t1 of the photo-excitation signal 705 shown in graph 700. The graph

710 depicts emitted acoustic waves (received wave (1) is one example) that may be received by an ultrasonic receiver array at an acquisition time delay RGD1 and sampled during an acquisition time window (also known as a range-gate window or a range-gate width) of RGW1. Such acoustic waves will generally be emitted from a relatively shallower portion of a target object proximate, or positioned upon, a platen of the biometric system.

Graph 715 depicts emitted acoustic waves (received wave (2) is one example) that are received by the ultrasonic receiver array at an acquisition time delay RGD2 (with RGD2>RGD1) and sampled during an acquisition time window of RGW2. Such acoustic waves will generally be emitted from a relatively deeper portion of the target object. Graph 720 depicts emitted acoustic waves (received wave (n) is one example) that are received at an acquisition time delay RGDn (with RGDn>RGD2>RGD1) and sampled during an acquisition time window of RGWn. Such acoustic waves will generally be emitted from a still deeper portion of the target object. Range-gate delays are typically integer multiples of a clock period. A clock frequency of 128 MHz, for example, has a clock period of 7.8125 nanoseconds, and RGDs may range from under 10 nanoseconds to over 2000 nanoseconds. Similarly, the range-gate widths may also be integer multiples of the clock period, but are often much shorter than the RGD (e.g. less than about 50 nanoseconds) to capture returning signals while retaining good axial resolution. In some implementations, the acquisition time window (e.g. RGW) may be between less than about 10 nanoseconds to about 200 nanoseconds or more. Note that while various image bias levels (e.g. Tx block, Rx sample and Rx hold that may be applied to an Rx bias electrode) may be in the single or low double-digit volt range, the return signals may have voltages in the tens or hundreds of millivolts.

Figure 8:
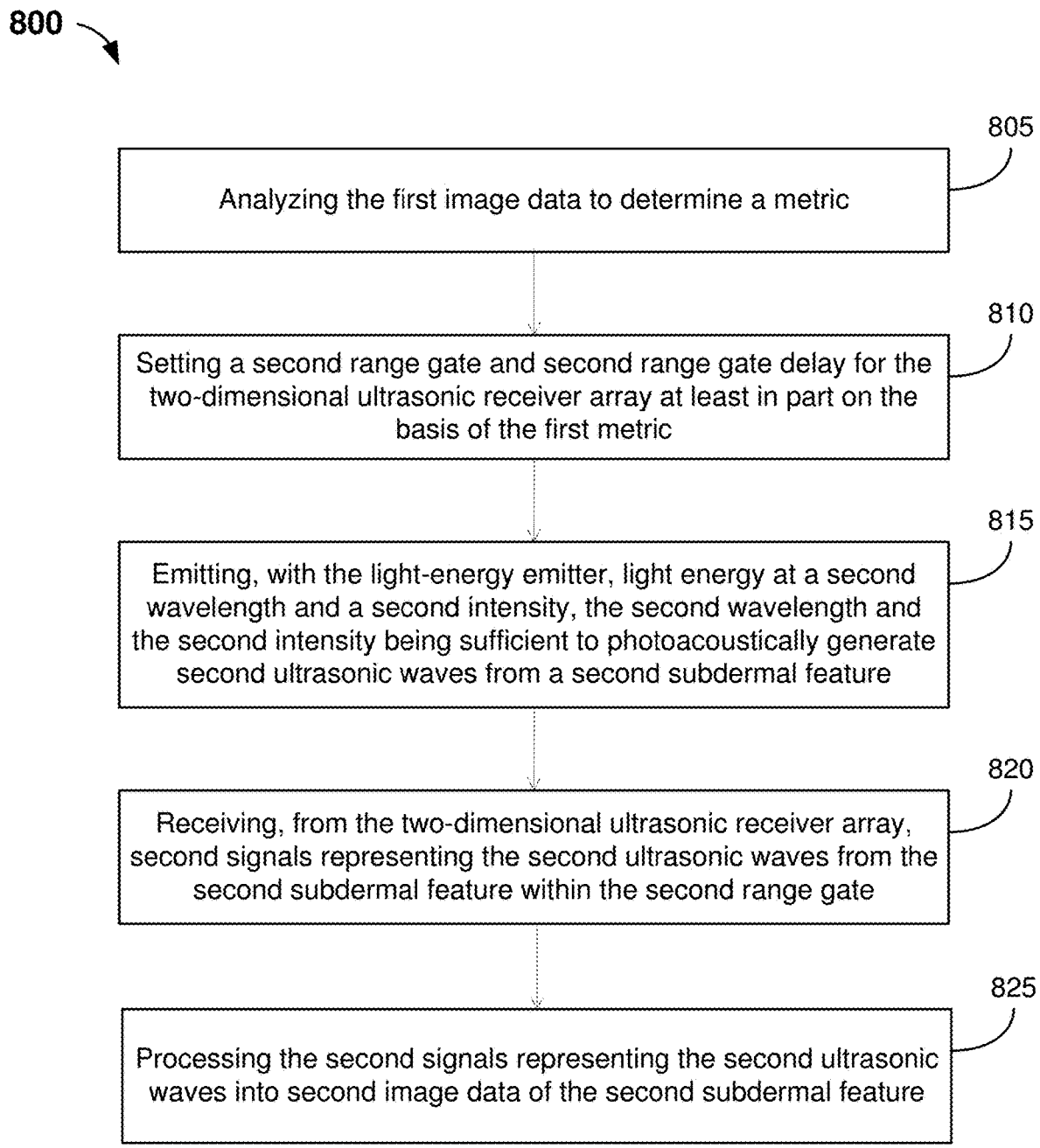
FIG. 8 is a flow diagram that provides additional examples of biometric system operations.

FIG. 8 is a flow diagram that provides additional examples of biometric system operations. The blocks of FIG. 8 (and those of other flow diagrams provided herein) may, for example, be performed by the apparatus 200 of FIG. 2 or by a similar apparatus. As with other methods disclosed herein, the method outlined in FIG. 8 may include more or fewer blocks than indicated. Moreover, the blocks of method 800, as well as other methods disclosed herein, are not necessarily performed in the order indicated.

Here, block 805 involves analyzing the first image data to determine a metric. Such a metric may be an indication of image quality, a depth of a subdermal feature, an indication of image intensity, or any other metric determined by an analysis of the first image data.

In an implementation, block 810 involves setting a second range gate and second range gate delay for the two-dimensional ultrasonic receiver array at least in part on the basis of the first metric. For example, the first metric may indicate that a deeper or shallower subdermal feature should be analyzed, or a first metric indicates that the light wavelength and intensity is not sufficient to provide a suitable image, and therefore the wavelength and intensity should be modified, as in block 815, which involves emitting, with the light-energy emitter, light energy at a second wavelength and a second intensity, the second wavelength and the second intensity being sufficient to photoacoustically generate second ultrasonic waves from a second subdermal feature. Block 820 involves receiving, from the two-dimensional ultrasonic receiver array, second signals representing the second ultrasonic waves from the second subdermal feature within the second range gate. These signals may be processed in block 825 which involves processing the second signals representing the second ultrasonic waves into second image data of the second subdermal feature.

Figure 9:
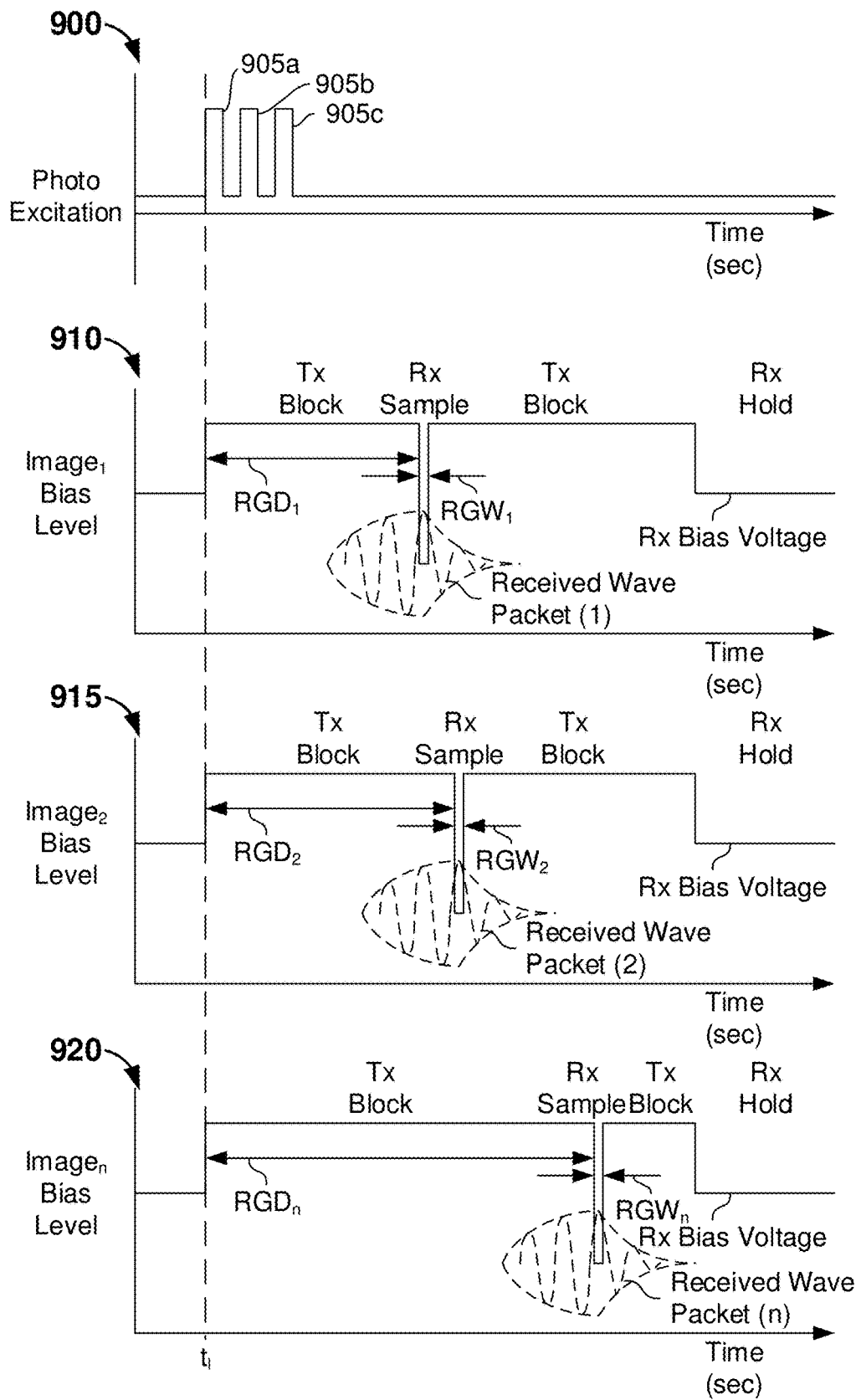
FIG. 9 shows examples of multiple acquisition time delays being selected to receive ultrasonic waves emitted from different depths, in response to a plurality of light pulses.

FIG. 9 shows examples of multiple acquisition time delays being selected to receive ultrasonic waves emitted from different depths, in response to a plurality of light pulses. In these examples, each of the acquisition time delays (which are labeled RGDs in FIG. 9) is measured from the beginning time t1 of the photo-excitation signal 905a as shown in graph 900. Accordingly, the examples of FIG. 9 are similar to those of FIG. 7. However, in FIG. 9, the photo-excitation signal 905a is only the first of multiple photo-excitation signals. In this example, the multiple photo-excitation signals include the photo-excitation signals 905b and 905c, for a total of three photo-excitation signals. In other implementations, a control system may control a light-energy emitter to emit more or fewer photo-excitation signals. In some implementations, the control system may be capable of controlling the light-energy emitter to emit a plurality of light pulses at a frequency between about 1 MHz and about 100 MHz.

The graph 910 illustrates ultrasonic waves (received wave packet (1) is one example) that are received by an ultrasonic receiver array at an acquisition time delay RGD1 and sampled during an acquisition time window of RGW1. Such ultrasonic waves will generally be emitted from a relatively shallower portion of a target object proximate to, or positioned upon, a platen of the subdermal imaging system. By comparing received wave packet (1) with received wave (1) of FIG. 7, it may be seen that the received wave packet (1) has a relatively longer time duration and a higher amplitude buildup than that of received wave (1) of FIG. 7. This longer time duration corresponds with the multiple photo-excitation signals in the examples shown in FIG. 9, as compared to the single photo-excitation signal in the examples shown in FIG. 7.

Graph 915 illustrates ultrasonic waves (received wave packet (2) is one example) that are received by the ultrasonic receiver array at an acquisition time delay RGD2 (with RGD2>RGD1) and sampled during an acquisition time window of RGW2. Such ultrasonic waves will generally be emitted from a relatively deeper portion of the target object. Graph 920 illustrates ultrasonic waves (received wave packet (n) is one example) that are received at an acquisition time delay RGDn (with RGDn>RGD2>RGD1) and sampled during an acquisition time window of RGWn. Such ultrasonic waves will generally be emitted from still deeper portions of the target object.

Figure 10A:
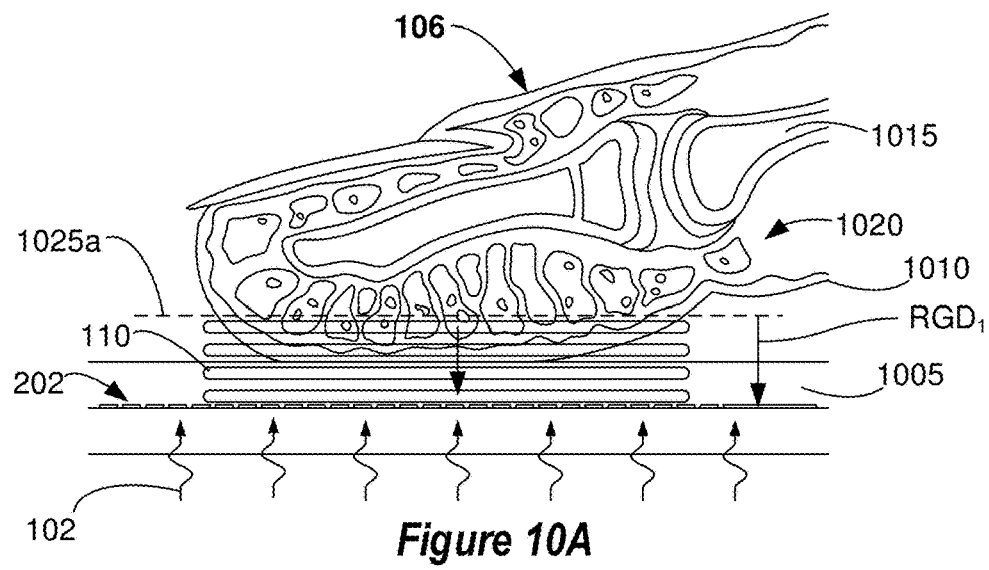
FIGS. 10A-10C are examples of cross-sectional views of a target object positioned on a platen of a subdermal imaging system such as those disclosed herein.
Figure 10B:
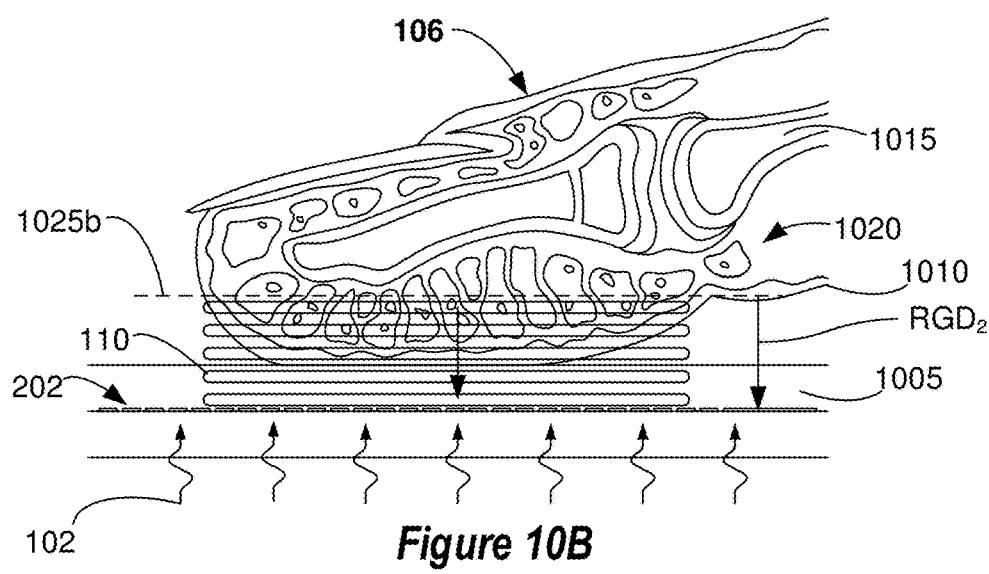
Figure 10C:
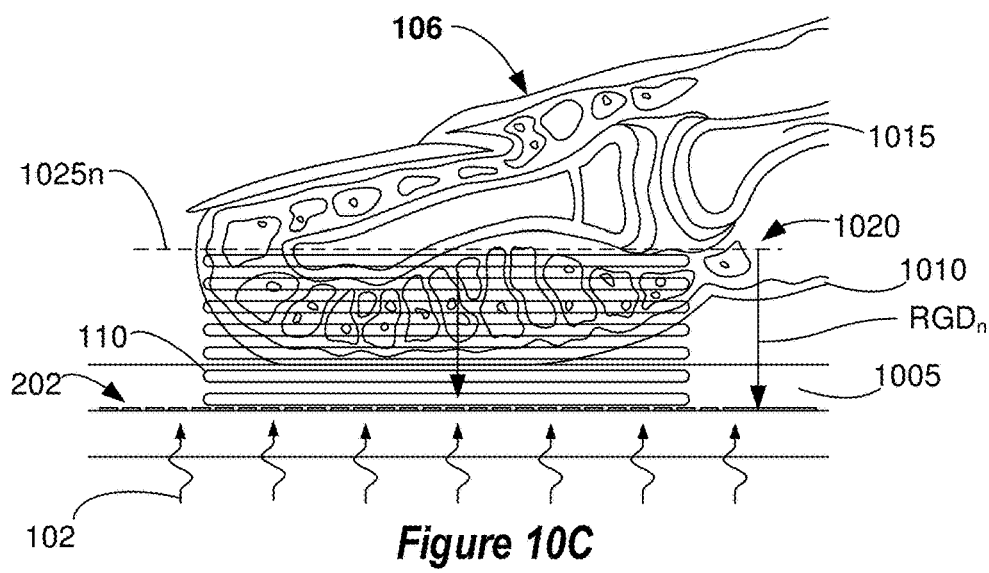

FIGS. 10A-10C are examples of cross-sectional views of a target object positioned on a platen of a biometric system such as those disclosed herein. In this example, the target object is a finger 106, which is positioned on an outer surface of a platen 1005. FIGS. 10A-10C show examples of tissues and structures of the finger 106, including the epidermis 1010, bone tissue 1015, blood vasculature 1020 and various sub-epidermal tissues. In this example, incident light 102 has been transmitted from a light-energy emitter (not shown) through the platen 1005 and into the finger 106. Here, the incident light 102 has caused optical excitation of the epidermis 1010 and blood vasculature 1020 and resultant generation of acoustic waves 110, which can be detected by the ultrasonic receiver array 202.

FIGS. 10A-10C indicate ultrasonic image data being acquired at three different range-gate delays (RGD1, RGD2 and RGDn), which are also referred to herein as acquisition time delays, after the beginning of a time interval of photo excitation. The dashed horizontal lines 1025a, 1025b and 1025n in FIGS. 10A-10C indicate the depth of each corresponding image. In some examples the photo excitation may be a single pulse (e.g., as shown in FIG. 7), whereas in other examples the photo excitation may include multiple pulses (e.g., as shown in FIG. 9). FIG. 10D is a cross-sectional view of the target object illustrated in FIGS. 10A-10C showing the image planes 1025a, 1025b, ... 1025n at varying depths through which image data has been acquired.

FIG. 10E shows a series of simplified two-dimensional images that correspond with ultrasonic image data acquired by the processes shown in FIGS. 10A-10C with reference to the image planes 1025a, 1025b and 1025n as shown in FIG. 10D. The two-dimensional images shown in FIG. 10E provide examples of two-dimensional images corresponding with ultrasonic image data that a control system could, in some implementations, cause a display device to display.

Image1 of FIG. 10E corresponds with the ultrasonic image data acquired using RGD1, which corresponds with the depth 1025a shown in FIGS. 10A and 10D. Image1 includes a portion of the epidermis 1010 and blood vasculature 1020 and also indicates structures of the sub-epidermal tissues.

Image2 corresponds with ultrasonic image data acquired using RGD2, which corresponds with the depth 1025b shown in FIGS. 10B and 10D. Image2 also includes a portion of the epidermis 1010, blood vasculature 1020 and indicates some additional structures of the sub-epidermal tissues.

Imagen corresponds with ultrasonic image data acquired using RGDn, which corresponds with the depth 1025n shown in FIGS. 10C and 10D. Imagen includes a portion of the epidermis 1010, blood vasculature 1020, some additional structures of the sub-epidermal tissues and structures corresponding to bone tissue 1015. Imagen also includes structures 1030 and 1032, which may correspond to bone tissue 1015 and/or to connective tissue near the bone tissue 1015, such as cartilage. However, it is not clear from Image1, Image2 or Imagen what the structures of the blood vasculature 1020 and sub-epidermal tissues are or how they relate to one another.

These relationships may be more clearly seen the three-dimensional image shown in FIG. 10F. FIG. 10F shows a composite of Image1, Image2 and Imagen, as well as additional images corresponding to depths that are between depth 1025b and depth 1025n. A three-dimensional image may be made from a set of two-dimensional images according to various methods known by those of skill in the art, such as a MATLAB® reconstruction routine or other routine that enables reconstruction or estimations of three-dimensional structures from sets of two-dimensional layer data. These routines may use spline-fitting or other curve-fitting routines and statistical techniques with interpolation to provide approximate contours and shapes represented by the two-dimensional ultrasonic image data. As compared to the two-dimensional images shown in FIG. 10E, the three-dimensional image shown in FIG. 10F more clearly represents structures corresponding to bone tissue 1015 as well as sub-epidermal structures including blood vasculature 1020, revealing vein, artery and capillary structures and other vascular structures along with bone shape, size and features.

Figure 11:
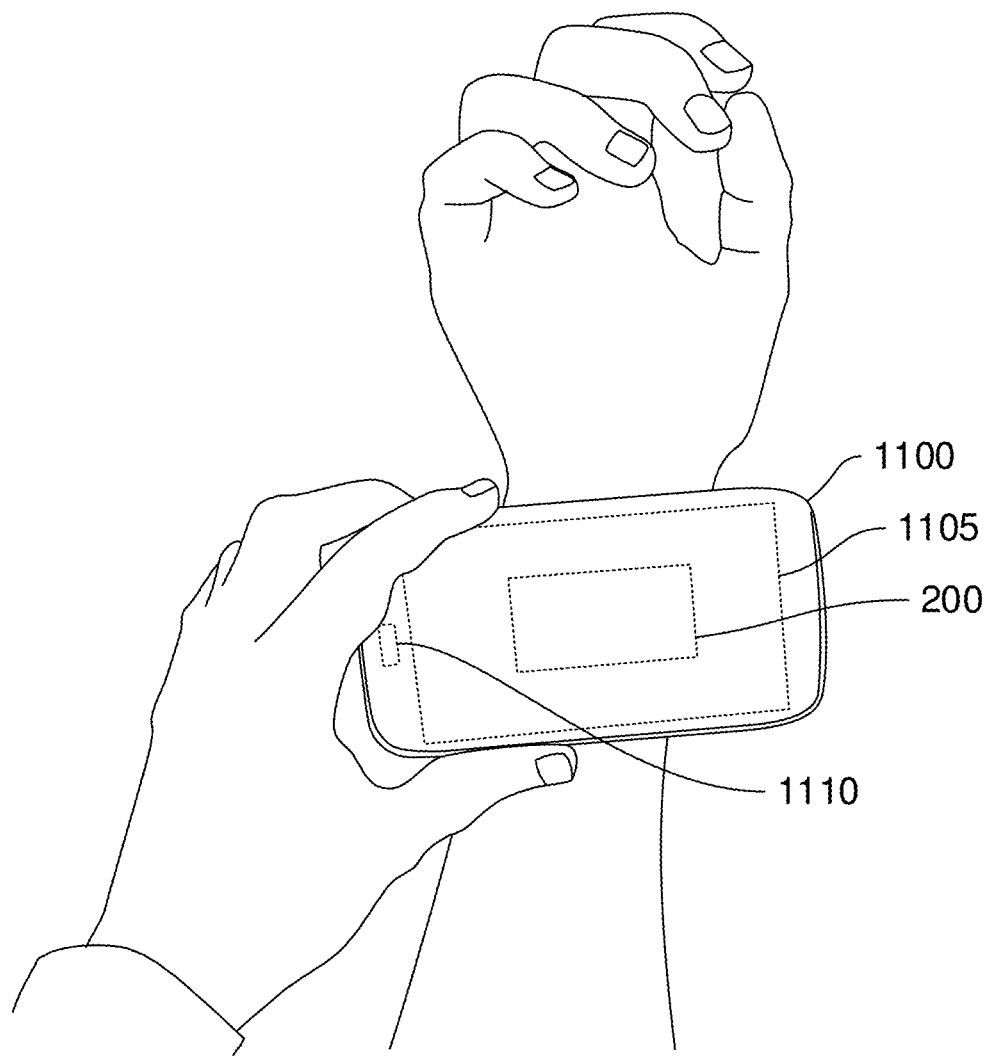
FIG. 11 shows an example of a mobile device that includes a biometric system capable of performing methods disclosed herein.

FIG. 11 shows an example of a mobile device that includes a biometric system capable of performing methods disclosed herein. A mobile device that includes such a biometric system may be capable of various types of mobile health monitoring, such as the imaging of blood vessel patterns, the analysis of blood and tissue components, etc.

In this example, the mobile device 1100 includes an instance of the apparatus 200 that is capable of functioning as an in-display photoacoustic imager (PAI). The apparatus 200 may, for example, be capable of emitting light that induces acoustic wave emissions inside a target object and acquiring ultrasonic image data from acoustic wave emissions received by an ultrasonic receiver array. In some examples, the apparatus 200 may be capable of acquiring ultrasonic image data during one or more acquisition time windows that are initiated at the end time of one or more acquisition time delays.

According to some implementations, the mobile device 1100 may be capable of displaying two-dimensional and/or three-dimensional images on the display 1105 that correspond with ultrasonic image data obtained via the apparatus 200. In other implementations, the mobile device may transmit ultrasonic image data (and/or attributes obtained from ultrasonic image data) to another device for processing and/or display.

In some examples, a control system of the mobile device 1100 (which may include a control system of the apparatus 200) may be capable of selecting one or more wavelengths of the light emitted by the apparatus 200. In some examples, the control system may be capable of selecting one or more wavelengths of light to trigger acoustic wave emissions primarily from a particular type of material in the target object. According to some implementations, the control system may be capable of estimating a blood oxygen level and/or of estimating a blood glucose level. In some implementations, the control system may be capable of selecting one or more wavelengths of light according to user input. For example, the mobile device 1100 may allow a user or a specialized software application to enter values corresponding to one or more wavelengths of the light emitted by the apparatus 200. Alternatively, or additionally, the mobile device 1100 may allow a user to select a desired function (such as estimating a blood oxygen level) and may determine one or more corresponding wavelengths of light to be emitted by the apparatus 200. For example, in some implementations, a wavelength in the mid-infrared region of the electromagnetic spectrum may be selected and a set of ultrasonic image data may be acquired in the vicinity of blood inside a blood vessel within a target object such as a finger or wrist. A second wavelength in another portion of the infrared region (e.g. near IR region) or in a visible region such as a red wavelength may be selected and a second set of ultrasonic image data may be acquired in the same vicinity as the first ultrasonic image data. A comparison of the first and second sets of ultrasonic image data, in conjunction with image data from other wavelengths or combinations of wavelengths, may allow an estimation of the blood glucose levels and/or blood oxygen levels within the target object.

In some implementations, a light-energy emitter of the mobile device 1100 may include at least one backlight or front light configured for illuminating the display 1105 and a target object. For example, the light-energy emitter may include one or more laser diodes, semiconductor lasers or light-emitting diodes. In some examples, the light-energy emitter may include at least one infrared, optical, red, green, blue, white or ultraviolet light-emitting diode or at least one infrared, optical, red, green, blue or ultraviolet laser diode. According to some implementations, the control system may be capable of controlling the light-energy emitter to emit at least one light pulse having a duration that is in the range of about 10 nanoseconds to about 500 nanoseconds. In some instances, the control system may be capable of controlling the light-energy emitter to emit a plurality of light pulses at a frequency between about 1 MHz and about 100 MHz.

In this example, the mobile device 1100 may include an ultrasonic authenticating button 1110 that includes another instance of the apparatus 200 that is capable of performing a user authentication process. In some such examples, the ultrasonic authenticating button 1110 may include an ultrasonic transmitter. According to some examples, the user authentication process may involve obtaining ultrasonic image data via insonification of a target object with ultrasonic waves from an ultrasonic transmitter and obtaining ultrasonic image data via illumination of the target object with light emitted from the light-energy emitter. In some such implementations, the ultrasonic image data obtained via insonification of the target object may include fingerprint image data and the ultrasonic image data obtained via illumination of the target object may include image data corresponding to one or more sub-epidermal features, such as vascular image data.

In this implementation, both the display 1105 and the apparatus 200 are on the side of the mobile device that is facing a target object, which is a wrist in this example, which may be imaged via the apparatus 200. However, in alternative implementations, the apparatus 200 may be on the opposite side of the mobile device 1100. For example, the display 1105 may be on the front of the mobile device and the apparatus 200 may be on the back of the mobile device. According to some such implementations, the mobile device may be capable of displaying two-dimensional and/or three-dimensional images, analogous to those shown in FIGS. 10E and 10F, as the corresponding ultrasonic image data are being acquired.

In some implementations, a portion of a target object, such as a wrist or arm, may be scanned as the mobile device 1100 is moved. According to some such implementations, a control system of the mobile device 1100 may be capable of stitching together the scanned images to form a more complete and larger two-dimensional or three-dimensional image. In some examples, the control system may be capable of acquiring first and second ultrasonic image data at primarily a first depth inside a target object. The second ultrasonic image data may be acquired after the target object or the mobile device 1100 is repositioned. In some implementations, the second ultrasonic image data may be acquired after a period of time corresponding to a frame rate, such as a frame rate between about one frame per second and about thirty frames per second or more. According to some such examples, the control system may be capable of stitching together or otherwise assembling the first and second ultrasonic image data to form a composite ultrasonic image.

Figure 12:
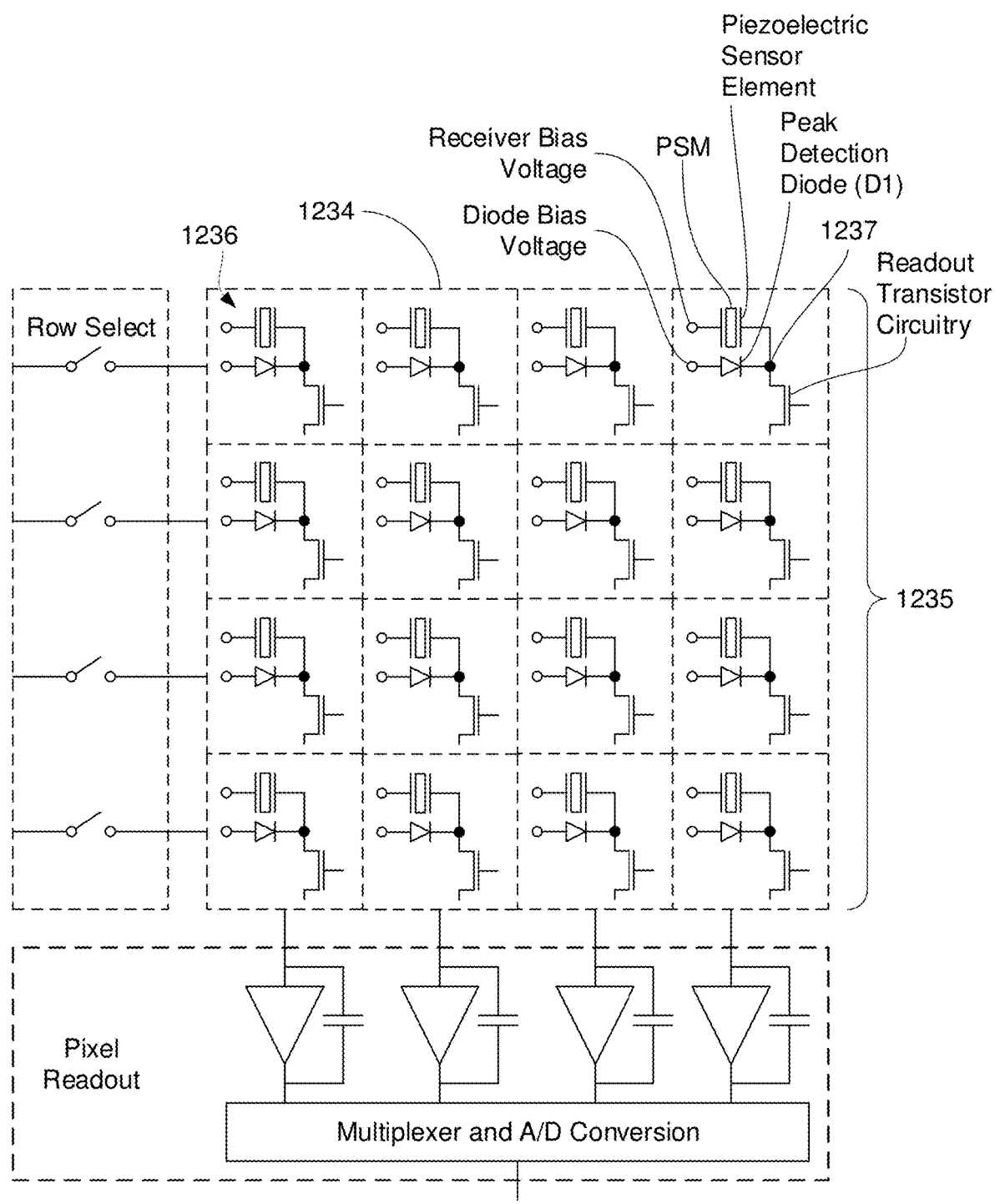
FIG. 12 representationally depicts aspects of a 4×4 pixel array of sensor pixels for an ultrasonic receiver system.

FIG. 12 representationally depicts aspects of a 4×4 pixel array 1235 of sensor pixels 1234 for an ultrasonic receiver system. Each pixel 1234 may be, for example, associated with a local region of piezoelectric sensor material (PSM), a peak detection diode (D1) and a readout transistor 1237; many or all of these elements may be formed on or in a substrate to form the pixel circuit 1236. In practice, the local region of piezoelectric sensor material of each pixel 1234 may transduce received ultrasonic energy into electrical charges. The peak detection diode D1 may register the maximum amount of charge detected by the local region of piezoelectric sensor material PSM. Each row of the pixel array 1235 may then be scanned, e.g., through a row select mechanism, a gate driver, or a shift register, and the readout transistor 1237 for each column may be triggered to allow the magnitude of the peak charge for each pixel 1234 to be read by additional circuitry, e.g., a multiplexer and an A/D converter. The pixel circuit 1236 may include one or more TFTs to allow gating, addressing, and resetting of the pixel 1234.

Each pixel circuit 1236 may provide information about a small portion of the object detected by the ultrasonic receiver system. While, for convenience of illustration, the example shown in FIG. 12 is of a relatively coarse resolution, ultrasonic receivers having a resolution on the order of 500 pixels per inch or higher may be configured with an appropriately scaled structure. The detection area of the ultrasonic receiver system may be selected depending on the intended object of detection. For example, the detection area may range from about 5 mm×5 mm for a single finger to about 3 inches×3 inches for four fingers. Smaller and larger areas, including square, rectangular and non-rectangular geometries, may be used as appropriate for the target object.

Figure 13A:
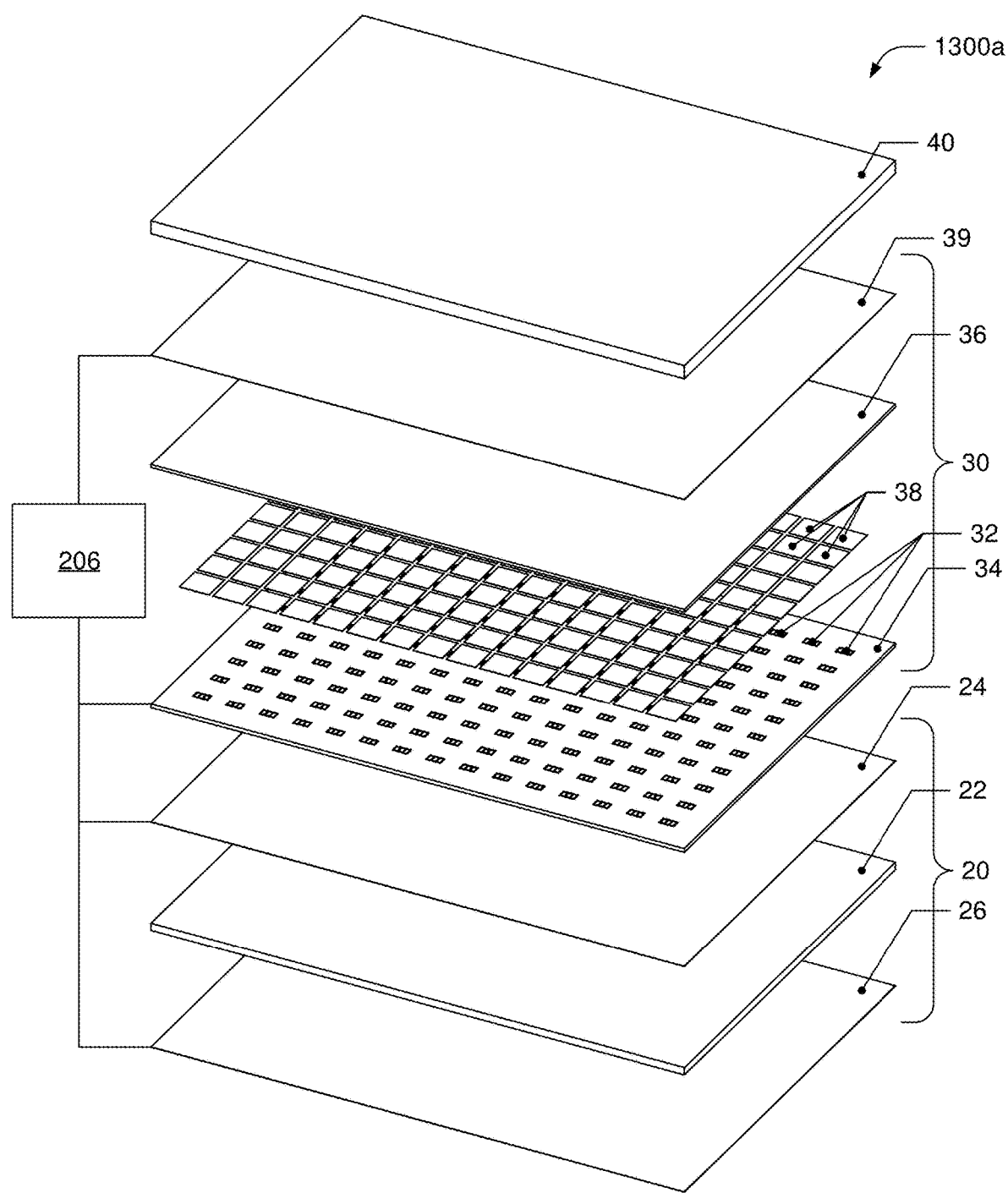
FIG. 13A shows an example of an exploded view of an ultrasonic receiver system.

FIG. 13A shows an example of an exploded view of an ultrasonic receiver system. In this example, the ultrasonic receiver system 1300*a* includes an ultrasonic transmitter 20 and an ultrasonic receiver 30 under a platen 40. According to some implementations, the ultrasonic receiver 30 may be an example of the ultrasonic receiver array 202 that is shown in FIG. 2 and described above. In some implementations, the ultrasonic transmitter 20 may be an example of the optional ultrasonic transmitter 208 that is shown in FIG. 2 and described above. The ultrasonic transmitter 20 may include a substantially planar piezoelectric transmitter layer 22 and may be capable of functioning as a plane wave generator. Ultrasonic waves may be generated by applying a voltage to the piezoelectric layer to expand or contract the layer, depending upon the signal applied, thereby generating a plane wave. In this example, the control system 206 may be capable of causing a voltage that may be applied to the planar piezoelectric transmitter layer 22 via a first transmitter electrode 24 and a second transmitter electrode 26. In this fashion, an ultrasonic wave may be made by changing the thickness of the layer via a piezoelectric effect. This ultrasonic wave may travel towards a finger (or other object to be detected), passing through the platen 40. A portion of the wave not absorbed or transmitted by the object to be detected may be reflected so as to pass back through the platen 40 and be received by the ultrasonic receiver 30. The first and second transmitter electrodes 24 and 26 may be metallized electrodes, for example, metal layers that coat opposing sides of the piezoelectric transmitter layer 22.

The ultrasonic receiver 30 may include an array of sensor pixel circuits 32 disposed on a substrate 34, which also may be referred to as a backplane, and a piezoelectric receiver layer 36. In some implementations, each sensor pixel circuit 32 may include one or more TFT elements, electrical interconnect traces and, in some implementations, one or more additional circuit elements such as diodes, capacitors, and the like. Each sensor pixel circuit 32 may be configured to convert an electric charge generated in the piezoelectric receiver layer 36 proximate to the pixel circuit into an electrical signal. Each sensor pixel circuit 32 may include a pixel input electrode 38 that electrically couples the piezoelectric receiver layer 36 to the sensor pixel circuit 32.

In the illustrated implementation, a receiver bias electrode 39 is disposed on a side of the piezoelectric receiver layer 36 proximal to platen 40. The receiver bias electrode 39 may be a metallized electrode and may be grounded or biased to control which signals may be passed to the array of sensor pixel circuits 32. Ultrasonic energy that is reflected from the exposed (top) surface of the platen 40 may be converted into localized electrical charges by the piezoelectric receiver layer 36. These localized charges may be collected by the pixel input electrodes 38 and passed on to the underlying sensor pixel circuits 32. The charges may be amplified or buffered by the sensor pixel circuits 32 and provided to the control system 206.

The control system 206 may be electrically connected (directly or indirectly) with the first transmitter electrode 24 and the second transmitter electrode 26, as well as with the receiver bias electrode 39 and the sensor pixel circuits 32 on the substrate 34. In some implementations, the control system 206 may operate substantially as described above. For example, the control system 206 may be capable of processing the amplified signals received from the sensor pixel circuits 32.

The control system 206 may be capable of controlling the ultrasonic transmitter 20 and/or the ultrasonic receiver 30 to obtain ultrasonic image data, e.g., by obtaining fingerprint images. Whether or not the ultrasonic receiver system 1300a includes an ultrasonic transmitter 20, the control system 206 may be capable of obtaining attribute information from the ultrasonic image data. In some examples, the control system 206 may be capable of controlling access to one or more devices based, at least in part, on the attribute information. The ultrasonic receiver system 1300a (or an associated device) may include a memory system that includes one or more memory devices. In some implementations, the control system 206 may include at least a portion of the memory system. The control system 206 may be capable of obtaining attribute information from ultrasonic image data and storing the attribute information in the memory system. In some implementations, the control system 206 may be capable of capturing a fingerprint image, obtaining attribute information from the fingerprint image and storing attribute information obtained from the fingerprint image (which may be referred to herein as fingerprint image information) in the memory system. According to some examples, the control system 206 may be capable of capturing a fingerprint image, obtaining attribute information from the fingerprint image and storing attribute information obtained from the fingerprint image even while maintaining the ultrasonic transmitter 20 in an "off" state.

In some implementations, the control system 206 may be capable of operating the ultrasonic receiver system 1300a in an ultrasonic imaging mode or a force-sensing mode. In some implementations, the control system may be capable of maintaining the ultrasonic transmitter 20 in an "off" state when operating the ultrasonic receiver system in a force-sensing mode. The ultrasonic receiver 30 may be capable of functioning as a force sensor when the ultrasonic receiver system 1300a is operating in the force-sensing mode. In some implementations, the control system 206 may be capable of controlling other devices, such as a display system, a communication system, etc. In some implementations, the control system 206 may be capable of operating the ultrasonic receiver system 1300a in a capacitive imaging mode.

The platen 40 may be any appropriate material that can be acoustically coupled to the receiver, with examples including plastic, ceramic, sapphire, metal and glass. In some implementations, the platen 40 may be a cover plate, e.g., a cover glass or a lens glass for a display. Particularly when the ultrasonic transmitter 20 is in use, fingerprint detection and imaging can be performed through relatively thick platens if desired, e.g., 3 mm and above. However, for implementations in which the ultrasonic receiver 30 is capable of imaging fingerprints in a force detection mode or a capacitance detection mode, a thinner and relatively more compliant platen 40 may be desirable. According to some such implementations, the platen 40 may include one or more polymers, such as one or more types of parylene, and may be substantially thinner. In some such implementations, the platen 40 may be tens of microns thick or even less than 10 microns thick.

Examples of piezoelectric materials that may be used to form the piezoelectric receiver layer 36 include piezoelectric polymers having appropriate acoustic properties, for example, an acoustic impedance between about 2.5 MRayls and 5 MRayls. Specific examples of piezoelectric materials that may be employed include ferroelectric polymers such as polyvinylidene fluoride (PVDF) and polyvinylidene fluoride-trifluoroethylene (PVDF-TrFE) copolymers. Examples of PVDF copolymers include 60:40 (molar percent) PVDF-TrFE, 70:30 PVDF-TrFE, 80:20 PVDF-TrFE, and 90:10 PVDR-TrFE. Other examples of piezoelectric materials that may be employed include polyvinylidene chloride (PVDC) homopolymers and copolymers, polytetrafluoroethylene (PTFE) homopolymers and copolymers, and diisopropylammonium bromide (DIPAB).

The thickness of each of the piezoelectric transmitter layer 22 and the piezoelectric receiver layer 36 may be selected so as to be suitable for generating and receiving ultrasonic waves. In one example, a PVDF planar piezoelectric transmitter layer 22 is approximately 28 μm thick and a PVDF-TrFE, receiver layer 36 is approximately 12 μm thick. Example frequencies of the ultrasonic waves may be in the range of 5 MHz to 30 MHz, with wavelengths on the order of a millimeter or less.

Figure 13B:
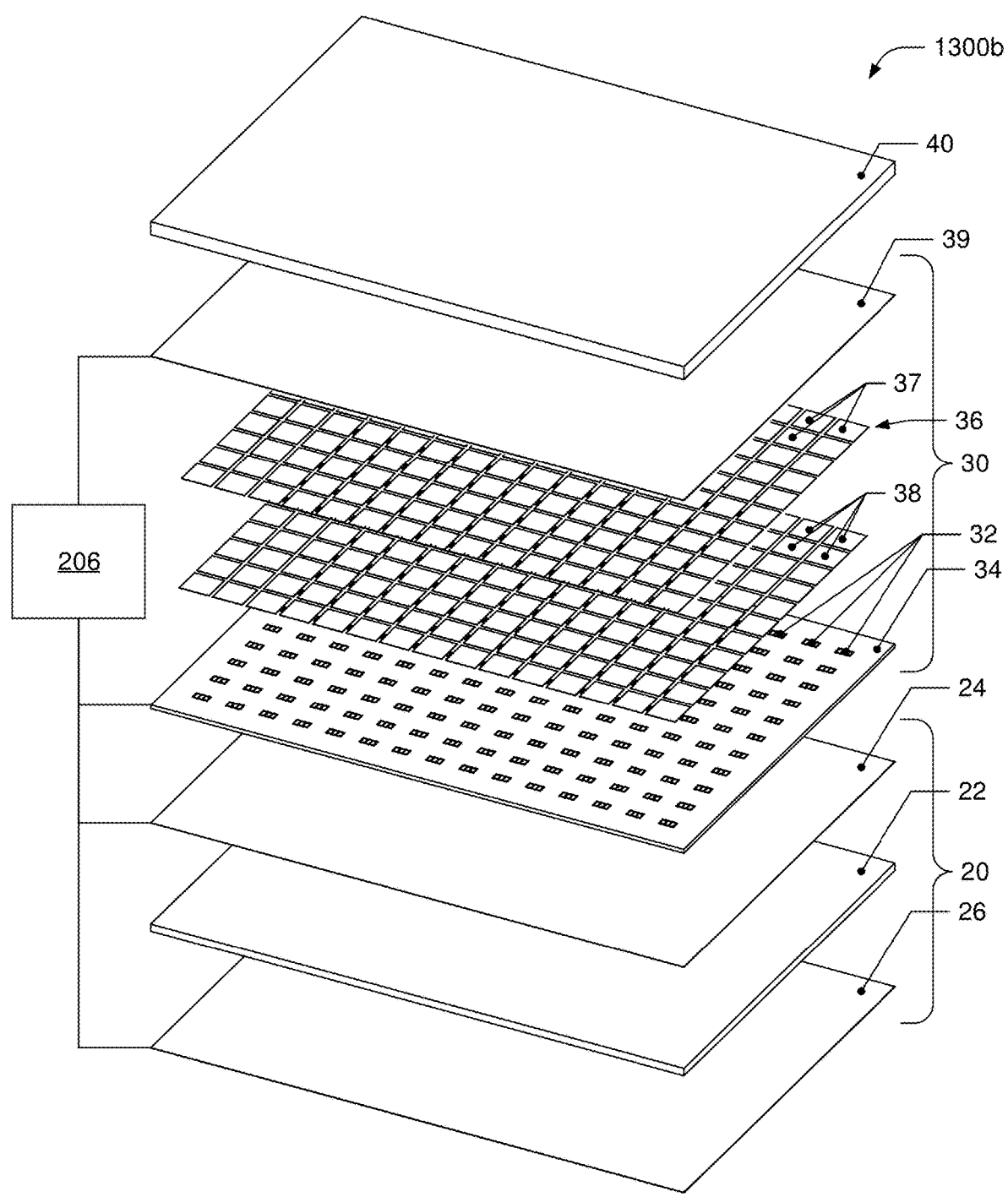
FIG. 13B shows an exploded view of an alternative example of an ultrasonic receiver system.

FIG. 13B shows an exploded view of an alternative example of an ultrasonic receiver system. In this example, the piezoelectric receiver layer 36 has been formed into discrete elements 37. In the implementation shown in FIG. 13B, each of the discrete elements 37 corresponds with a single pixel input electrode 38 and a single sensor pixel circuit 32. However, in alternative implementations of the ultrasonic receiver system 1300b, there is not necessarily a one-to-one correspondence between each of the discrete elements 37, a single pixel input electrode 38 and a single sensor pixel circuit 32. For example, in some implementations there may be multiple pixel input electrodes 38 and sensor pixel circuits 32 for a single discrete element 37.

FIGS. 13A and 13B show example arrangements of ultrasonic transmitters and receivers in an ultrasonic receiver system, with other arrangements possible. For example, in some implementations, the ultrasonic transmitter 20 may be above the ultrasonic receiver 30 and therefore closer to the object(s) 25 to be detected. In some implementations, the ultrasonic transmitter may be included with the ultrasonic receiver array (e.g., a single-layer transmitter and receiver). In some implementations, the ultrasonic receiver system may include an acoustic delay layer. For example, an acoustic delay layer may be incorporated into the ultrasonic receiver system between the ultrasonic transmitter 20 and the ultrasonic receiver 30. An acoustic delay layer may be employed to adjust the ultrasonic pulse timing, and at the same time electrically insulate the ultrasonic receiver 30 from the ultrasonic transmitter 20. The acoustic delay layer may have a substantially uniform thickness, with the material used for the delay layer and/or the thickness of the delay layer selected to provide a desired delay in the time for reflected ultrasonic energy to reach the ultrasonic receiver 30. In doing so, the range of time during which an energy pulse that carries information about the object by virtue of having been reflected by the object may be made to arrive at the ultrasonic receiver 30 during a time range when it is unlikely that energy reflected from other parts of the ultrasonic receiver system is arriving at the ultrasonic receiver 30. In some implementations, the substrate 34 and/or the platen 40 may serve as an acoustic delay layer.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

What is claimed is:

1. An apparatus for subdermal imaging, the apparatus comprising:

a two-dimensional ultrasonic receiver array;
a light-energy emitter;
a display; and
a control system configured to:
  determine whether an object is in contact with the display;
  in response to a determination that the object is in contact with the display, cause the light-energy emitter to emit light-energy at a first wavelength and a first intensity, the first wavelength and the first intensity being sufficient to photoacoustically generate first ultrasonic waves from a first subdermal feature of the object;
  set a first range gate and a first range gate delay for the two-dimensional ultrasonic receiver array corresponding to a depth of the first subdermal feature;
  receive, from the two-dimensional ultrasonic receiver array, first signals representing the first ultrasonic waves from the first subdermal feature within the first range gate;
  process the first signals representing the first ultrasonic waves to generate first image data of the first subdermal feature;
  analyze the first image data to determine a first metric;
  set a second range gate and second range gate delay for the two-dimensional ultrasonic receiver array based at least in part on the first metric;
  cause the light-energy emitter to emit light-energy at a second wavelength and a second intensity, the second wavelength and the second intensity being sufficient to photoacoustically generate second ultrasonic waves from a second subdermal feature;
  receive, from the two-dimensional ultrasonic receiver array, second signals representing the second ultrasonic waves from the second subdermal feature within the second range gate; and
  process the second signals representing the first ultrasonic waves to generate second image data of the second subdermal feature.

2. The apparatus of claim 1, wherein the display is collocated with the two-dimensional ultrasonic receiver array.

3. The apparatus of claim 1, wherein the two-dimensional ultrasonic receiver array comprises a two-dimensional array of piezoelectric micromachined ultrasonic transducers (PMUTs).

4. The apparatus of claim 1, wherein the first metric is an indication of image quality, a depth of a subdermal feature or an indication of image intensity.

5. The apparatus of claim 1, wherein the second wavelength is different from the first wavelength, or the second intensity is different from the first intensity, or both.

6. The apparatus of claim 1, wherein the control system is further configured to:
  receive an input from a first sensor, the first sensor being different from the two-dimensional ultrasonic receiver array; and
  set the second range gate and second range gate delay for the two-dimensional ultrasonic receiver array based at least in part on the received input from the first sensor.

7. The apparatus of claim 6, wherein the second wavelength is different from the first wavelength, or the second intensity is different from the first intensity, or both.

8. The apparatus of claim 6, wherein the first sensor is a temperature sensor.

9. The apparatus of claim 1, wherein the control system is further configured to:
  determine a first distance to the first subdermal feature at least in part at least in part on the basis of the first range gate delay; and
  determine a second distance between a first portion of the first subdermal feature and a second portion of the first subdermal feature at least in part at least in part on the basis of the first distance.

10. The apparatus of claim 1, wherein the control system is further configured to:
  determine a first distance to the first subdermal feature at least in part on the basis of the first range gate delay;
  determine a second distance to the second subdermal feature at least in part on the basis of the second range gate delay; and
  determine a third distance between the first subdermal feature and the second subdermal feature at least in part at least in part on the basis of the first distance and the second distance.

11. A method for subdermal imaging, the method comprising:
  determining, by a control system, whether an object is in contact with a display;
  in response to a determination that the object is in contact with the display, emitting light-energy, by a light-energy emitter, at a first wavelength and a first intensity, the first wavelength and the first intensity being sufficient to photoacoustically generate first ultrasonic waves from a first subdermal feature;
  setting a first range gate and a first range gate delay, for a two-dimensional ultrasonic receiver array, corresponding to a depth of the first subdermal feature;
  receiving, from the two-dimensional ultrasonic receiver array, first signals representing the first ultrasonic waves from the first subdermal feature within the first range gate;
  processing the first signals representing the first ultrasonic waves to generate first image data of the first subdermal feature;
  analyzing the first image data to determine a first metric;
  setting a second range gate and second range gate delay for the two-dimensional ultrasonic receiver array based at least in part on the first metric;
  causing the light-energy emitter to emit light-energy at a second wavelength and a second intensity, the second wavelength and the second intensity being sufficient to photoacoustically generate second ultrasonic waves from a second subdermal feature;
  receiving, from the two-dimensional ultrasonic receiver array, second signals representing the second ultrasonic waves from the second subdermal feature within the second range gate; and
  processing the second signals representing the first ultrasonic waves to generate second image data of the second subdermal feature.

12. The method of claim 11, wherein the first metric is an indication of image quality, a depth of a subdermal feature or an indication of image intensity.

13. The method of claim 11, wherein the second wavelength is different from the first wavelength, or the second intensity is different from the first intensity, or both.

14. The method of claim 11, further comprising:
  receiving an input from a first sensor, the first sensor being different from the two-dimensional ultrasonic receiver array; and setting the second range gate and second range gate delay for the two-dimensional ultrasonic receiver array at least in part on the basis of the received input from the first sensor.

15. The method of claim 14, wherein the second wavelength is different from the first wavelength, or the second intensity is different from the first intensity, or both.

16. The method of claim 14, wherein the first sensor is a temperature sensor.

17. The method of claim 11, further comprising:
determining a first distance to the first subdermal feature at least in part at least in part on the basis of the first range gate delay; and
determining a second distance between a first portion of the first subdermal feature and a second portion of the first subdermal feature at least in part at least in part on the basis of the first distance.

18. The method of claim 12, wherein the control system is further configured to:
determine a first distance to the first subdermal feature at least in part on the basis of the first range gate delay;
determine a second distance to the second subdermal feature at least in part on the basis of the second range gate delay; and
determine a third distance between the first subdermal feature and the second subdermal feature at least in part at least in part on the basis of the first distance and the second distance.

19. A subdermal imager comprising:
means for determining whether an object is in contact with a display;
means for emitting light at a first wavelength and a first intensity, the first wavelength and the first intensity being sufficient to photoacoustically generate first ultrasonic waves from a first subdermal feature;
means for setting a first range gate and a first range gate delay, for a two-dimensional ultrasonic receiver array, corresponding to a depth of the first subdermal feature;
means for receiving first signals representing the first ultrasonic waves from the first subdermal feature within the first range gate;
means for processing the first signals representing the first ultrasonic waves to generate first image data of the first subdermal feature;
means for analyzing the first image data to determine a first metric;
means for setting a second range gate and second range gate delay for the two-dimensional ultrasonic receiver array based at least in part on the first metric;
means for causing the light-energy emitter to emit light-energy at a second wavelength and a second intensity, the second wavelength and the second intensity being sufficient to photoacoustically generate second ultrasonic waves from a second subdermal feature;
means for receiving, from the two-dimensional ultrasonic receiver array, second signals representing the second ultrasonic waves from the second subdermal feature within the second range gate; and
means for processing the second signals representing the first ultrasonic waves to generate second image data of the second subdermal feature.

20. The subdermal imager of claim 19, wherein the first metric is an indication of image quality, a depth of a subdermal feature or an indication of image intensity.

21. The subdermal imager of claim 20, wherein one or both of the second wavelength and the second intensity are different from the first wavelength and first intensity, respectively.

22. The subdermal imager of claim 19, further comprising:
means for receiving an input from a first sensor; and
means for setting the second range gate and second range gate delay for the two-dimensional ultrasonic receiver array at least in part on the basis of received input from the first sensor.

23. The subdermal imager of claim 22, wherein the second wavelength is different from the first wavelength, or the second intensity is different from the first intensity, or both.

24. The subdermal imager of claim 22, wherein the received input comprises a temperature reading.

25. The subdermal imager of claim 19, further comprising:
means for determining a first distance to the first subdermal feature at least in part at least in part on the basis of the first range gate delay; and
means for determining a second distance between a first portion of the first subdermal feature and a second portion of the first subdermal feature at least in part at least in part on the basis of the first distance.

26. The subdermal imager of claim 20, further comprising:
means for determining a first distance to the first subdermal feature at least in part on the basis of the first range gate delay;
means for determining a second distance to the second subdermal feature at least in part on the basis of the second range gate delay; and
means for determining a third distance between the first subdermal feature and the second subdermal feature at least in part at least in part on the basis of the first distance and the second distance.

* * * * *